US012708814B2

(12) United States Patent
Mason

(10) Patent No.: US 12,708,814 B2
(45) Date of Patent: Aug. 18, 2026

(54) SYSTEM AND METHOD FOR USING AN ARTIFICIAL INTELLIGENCE ENGINE TO ANONYMIZE COMPETITIVE PERFORMANCE RANKINGS IN A REHABILITATION SETTING

(71) Applicant: ROM TECHNOLOGIES, INC., Brookfield, CT (US)

(72) Inventor: Steven Mason, Las Vegas, NV (US)

(73) Assignee: ROM Technologies, Inc., Brookfield, CT (US)

( * ) Notice: Subject to any disclaimer, the term of this patent is extended or adjusted under 35 U.S.C. 154(b) by 1000 days.

(21) Appl. No.: 17/854,873

(22) Filed: Jun. 30, 2022

(65) Prior Publication Data

US 2022/0331663 A1 Oct. 20, 2022

Related U.S. Application Data

(63) Continuation-in-part of application No. 17/739,906, filed on May 9, 2022, now Pat. No. 12,558,594, (Continued)

(51) Int. Cl.
*A63B 24/00* (2006.01)
*A63B 21/005* (2006.01)
(Continued)

(52) U.S. Cl.
CPC ...... *A63B 24/0075* (2013.01); *A63B 21/0058* (2013.01); *A63B 24/0062* (2013.01);
(Continued)

(58) Field of Classification Search
CPC ........ A63B 2022/0094; A63B 24/0062; A63B 24/0075; G06N 20/00; G16H 10/60; G16H 20/30; G16H 50/20
See application file for complete search history.

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
(Continued)

*Primary Examiner* — Vincent H Tran
(74) *Attorney, Agent, or Firm* — Dickinson Wright PLLC; Jonathan H. Harder; Stephen A. Mason

(57) ABSTRACT

The present disclosure provides a method comprising the steps: receiving first patient data, wherein the first patient data includes at least a first patient identifier associated with the first patient and a first treatment plan including an exercise; receiving first measurement data, where the first measurement data is associated with a first performance data; receiving second measurement data, where the second measurement data is associated with at least one of a second performance data and a second patient identifier; one of anonymiztion of and pseudonymization of the second patient identifier; determining, via an artificial intelligence engine and based on one or more differences between the first and the second measurement data, differential data; and presenting, with a patient interface, at least one of the differential data, first measurement data, second measurement data, and the first patient data.

18 Claims, 10 Drawing Sheets

Related U.S. Application Data which is a continuation of application No. 17/150,938, filed on Jan. 15, 2021, now Pat. No. 11,325,005, which is a continuation-in-part of application No. 17/021,895, filed on Sep. 15, 2020, now Pat. No. 11,071,597.

(60) Provisional application No. 63/217,052, filed on Jun. 30, 2021, provisional application No. 62/910,232, filed on Oct. 3, 2019.

(51) Int. Cl.

| | |
|---|---|
| ***G06N 20/00*** | (2019.01) |
| ***G16H 10/60*** | (2018.01) |
| ***G16H 20/30*** | (2018.01) |
| *A63B 22/00* | (2006.01) |
| *A63B 22/06* | (2006.01) |

(52) U.S. Cl.

CPC ............ *G06N 20/00* (2019.01); *G16H 10/60* (2018.01); *G16H 20/30* (2018.01); *A63B 2022/0094* (2013.01); *A63B 22/0605* (2013.01); *A63B 2024/0093* (2013.01)

(56) References Cited

U.S. PATENT DOCUMENTS

| | | | |
|---|---|---|---|
| 4,822,032 | A | 4/1989 | Whitmore et al. |
| 4,860,763 | A | 8/1989 | Schminke |
| 4,869,497 | A | 9/1989 | Stewart et al. |
| 4,932,650 | A | 6/1990 | Bingham et al. |
| 5,137,501 | A | 8/1992 | Mertesdorf |
| 5,161,430 | A | 11/1992 | Febey |
| 5,202,794 | A | 4/1993 | Schnee et al. |
| 5,240,417 | A | 8/1993 | Smithson et al. |
| 5,247,853 | A | 9/1993 | Dalebout |
| 5,256,117 | A | 10/1993 | Potts et al. |
| D342,299 | S | 12/1993 | Birrell et al. |
| 5,282,748 | A | 2/1994 | Little |
| 5,284,131 | A | 2/1994 | Gray |
| 5,316,532 | A | 5/1994 | Butler |
| 5,318,487 | A | 6/1994 | Golen |
| 5,324,241 | A | 6/1994 | Artigues et al. |
| 5,336,147 | A | 8/1994 | Sweeney, III |
| 5,338,272 | A | 8/1994 | Sweeney, III |
| 5,356,356 | A | 10/1994 | Hildebrandt |
| 5,361,649 | A | 11/1994 | Slocum, Jr. |
| D359,777 | S | 6/1995 | Hildebrandt |
| 5,429,140 | A | 7/1995 | Burdea et al. |
| 5,458,022 | A | 10/1995 | Mattfeld et al. |
| 5,487,713 | A | 1/1996 | Butler |
| 5,566,589 | A | 10/1996 | Buck |
| 5,580,338 | A | 12/1996 | Scelta et al. |
| 5,676,349 | A | 10/1997 | Wilson |
| 5,685,804 | A | 11/1997 | Whan-Tong et al. |
| 5,738,636 | A | 4/1998 | Saringer et al. |
| 5,860,941 | A | 1/1999 | Saringer et al. |
| 5,950,813 | A | 9/1999 | Hoskins et al. |
| 6,007,459 | A | 12/1999 | Burgess |
| D421,075 | S | 2/2000 | Hildebrandt |
| 6,053,847 | A | 4/2000 | Stearns et al. |
| 6,077,201 | A | 6/2000 | Cheng |
| 6,102,834 | A | 8/2000 | Chen |
| 6,110,130 | A | 8/2000 | Kramer |
| 6,155,958 | A | 12/2000 | Goldberg |
| 6,162,189 | A | 12/2000 | Girone et al. |
| 6,182,029 | B1 | 1/2001 | Friedman |
| D438,580 | S | 3/2001 | Shaw |
| 6,253,638 | B1 | 7/2001 | Bermudez |
| 6,267,735 | B1 | 7/2001 | Blanchard et al. |
| 6,273,863 | B1 | 8/2001 | Avni et al. |
| D450,100 | S | 11/2001 | Hsu |
| D450,101 | S | 11/2001 | Hsu |
| D451,972 | S | 12/2001 | Easley |
| D452,285 | S | 12/2001 | Easley |
| D454,605 | S | 3/2002 | Lee |
| 6,371,891 | B1 | 4/2002 | Speas |
| D459,776 | S | 7/2002 | Lee |
| 6,413,190 | B1 | 7/2002 | Wood et al. |
| 6,430,436 | B1 | 8/2002 | Richter |
| 6,436,058 | B1 | 8/2002 | Krahner et al. |
| 6,450,923 | B1 | 9/2002 | Vatti |
| 6,474,193 | B1 | 11/2002 | Farney |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,543,309 | B2 | 4/2003 | Heim |
| 6,589,139 | B1 | 7/2003 | Butterworth |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,640,662 | B1 | 11/2003 | Baxter |
| 6,652,425 | B1 | 11/2003 | Martin et al. |
| 6,659,946 | B1 * | 12/2003 | Batchelor ............. G16H 20/60 128/920 |
| 6,820,517 | B1 | 11/2004 | Farney |
| 6,865,969 | B2 | 3/2005 | Stevens |
| 6,890,312 | B1 | 5/2005 | Priester et al. |
| 6,895,834 | B1 | 5/2005 | Baatz |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,204,788 | B2 | 4/2007 | Andrews |
| 7,209,886 | B2 | 4/2007 | Kimmel |
| 7,226,394 | B2 | 6/2007 | Johnson |
| RE39,904 | E | 10/2007 | Lee |
| 7,406,003 | B2 | 7/2008 | Burkhardt et al. |
| 7,507,188 | B2 | 3/2009 | Nurre |
| 7,594,879 | B2 | 9/2009 | Johnson |
| 7,628,730 | B1 | 12/2009 | Watterson et al. |
| D610,635 | S | 2/2010 | Hildebrandt |
| 7,778,851 | B2 | 8/2010 | Schoenberg et al. |
| 7,809,601 | B2 | 10/2010 | Shaya et al. |
| 7,815,551 | B2 | 10/2010 | Merli |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,988,599 | B2 | 8/2011 | Ainsworth et al. |
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell |
| 8,113,991 | B2 | 2/2012 | Kutliroff |
| 8,172,724 | B2 | 5/2012 | Solomon |
| 8,177,732 | B2 | 5/2012 | Einav et al. |
| 8,287,434 | B2 | 10/2012 | Zavadsky et al. |
| 8,298,123 | B2 | 10/2012 | Hickman |
| 8,371,990 | B2 | 2/2013 | Shea |
| 8,419,593 | B2 | 4/2013 | Ainsworth et al. |
| 8,465,398 | B2 | 6/2013 | Lee et al. |
| 8,503,086 | B2 | 8/2013 | French |
| 8,506,458 | B2 | 8/2013 | Dugan |
| 8,515,777 | B1 | 8/2013 | Rajasenan |
| 8,540,515 | B2 | 9/2013 | Williams et al. |
| 8,540,516 | B2 | 9/2013 | Williams et al. |
| 8,556,778 | B1 | 10/2013 | Dugan |
| 8,607,465 | B1 | 12/2013 | Edwards |
| 8,613,689 | B2 | 12/2013 | Dyer et al. |
| 8,615,529 | B2 | 12/2013 | Reiner |
| 8,672,812 | B2 | 3/2014 | Dugan |
| 8,751,264 | B2 | 6/2014 | Beraja et al. |
| 8,784,273 | B2 | 7/2014 | Dugan |
| 8,818,496 | B2 | 8/2014 | Dziubinski et al. |
| 8,823,448 | B1 | 9/2014 | Shen |
| 8,845,493 | B2 | 9/2014 | Watterson et al. |

(56) References Cited

U.S. PATENT DOCUMENTS 8,849,681 B2 9/2014 Hargrove et al.
8,864,628 B2 10/2014 Boyette et al.
8,893,287 B2 11/2014 Gjonej et al.
8,911,327 B1 12/2014 Boyette
8,979,711 B2 3/2015 Dugan
9,004,598 B2 4/2015 Weber
9,044,630 B1 6/2015 Lampert et al.
9,167,281 B2 10/2015 Petrov et al.
D744,050 S 11/2015 Colburn
9,248,071 B1 2/2016 Brenda
9,256,711 B2 2/2016 Horseman
9,272,091 B2 3/2016 Skelton
9,272,185 B2 3/2016 Dugan
9,283,434 B1 3/2016 Wu
9,295,878 B2 3/2016 Corbalis et al.
9,311,789 B1 4/2016 Gwin
9,312,907 B2 4/2016 Auchinleck et al.
9,367,668 B2 6/2016 Flynt et al.
9,409,054 B2 8/2016 Dugan
9,443,205 B2 9/2016 Wall
9,474,935 B2 10/2016 Abbondanza et al.
9,480,873 B2 11/2016 Chuang
9,481,428 B2 11/2016 Gros
9,514,277 B2 12/2016 Hassing et al.
9,566,472 B2 2/2017 Dugan
9,579,056 B2 2/2017 Rosenbek et al.
9,629,558 B2 4/2017 Yuen et al.
9,640,057 B1 5/2017 Ross
9,707,147 B2 7/2017 Levital et al.
9,713,744 B2 7/2017 Suzuki
D794,142 S 8/2017 Zhou
9,717,947 B2 8/2017 Lin
9,737,761 B1 8/2017 Govindarajan
9,757,612 B2 9/2017 Weber
9,773,330 B1 9/2017 Douglas
9,782,621 B2 10/2017 Chiang et al.
9,802,076 B2 10/2017 Murray et al.
9,802,081 B2 10/2017 Ridgel et al.
9,813,239 B2 11/2017 Chee et al.
9,827,445 B2 11/2017 Marcos et al.
9,849,337 B2 12/2017 Roman et al.
9,868,028 B2 1/2018 Shin
9,872,087 B2 1/2018 DelloStritto et al.
9,872,637 B2 1/2018 Kording et al.
9,914,053 B2 3/2018 Dugan
9,919,198 B2 3/2018 Romeo et al.
9,937,382 B2 4/2018 Dugan
9,939,784 B1 4/2018 Berardinelli
9,974,478 B1 5/2018 Brokaw
9,977,587 B2 5/2018 Mountain
9,993,181 B2 6/2018 Ross
9,997,082 B2 6/2018 Kaleal
10,004,946 B2 6/2018 Ross
10,026,052 B2 7/2018 Brown et al.
D826,349 S 8/2018 Oblamski
10,055,550 B2 8/2018 Goetz
10,058,473 B2 8/2018 Oshima et al.
10,074,148 B2 9/2018 Cashman et al.
10,089,443 B2 10/2018 Miller et al.
10,111,643 B2 10/2018 Shulhauser et al.
10,130,311 B1 11/2018 De Sapio et al.
10,137,328 B2 11/2018 Baudhuin
10,143,395 B2 12/2018 Chakravarthy et al.
10,155,134 B2 12/2018 Dugan
10,159,872 B2 12/2018 Sasaki et al.
10,173,094 B2 1/2019 Gomberg
10,173,095 B2 1/2019 Gomberg et al.
10,173,096 B2 1/2019 Gomberg et al.
10,173,097 B2 1/2019 Gomberg et al.
10,198,928 B1 2/2019 Ross et al.
10,226,663 B2 3/2019 Gomberg et al.
10,231,664 B2 3/2019 Ganesh
10,244,990 B2 4/2019 Hu et al.
10,258,823 B2 4/2019 Cole
10,322,315 B2 6/2019 Foley et al.
10,325,070 B2 6/2019 Beale et al.
10,327,697 B1 6/2019 Stein et al.
10,362,940 B2 7/2019 Tran
10,369,021 B2 8/2019 Zoss et al.
10,380,866 B1 8/2019 Ross et al.
10,413,222 B1 9/2019 Kayyall
10,413,238 B1 9/2019 Cooper
10,424,033 B2 9/2019 Romeo
10,430,552 B2 10/2019 Mihai
D866,957 S 11/2019 Ross et al.
10,468,131 B2 11/2019 Macoviak et al.
10,475,323 B1 11/2019 Ross
10,475,537 B2 11/2019 Purdie et al.
10,492,977 B2 12/2019 Kapure et al.
10,507,358 B2 12/2019 Kinnunen et al.
10,542,914 B2 1/2020 Forth et al.
10,546,467 B1 1/2020 Luciano, Jr. et al.
10,569,122 B2 2/2020 Johnson
10,572,626 B2 2/2020 Balram
10,576,331 B2 3/2020 Kuo
10,581,896 B2 3/2020 Nachenberg
10,625,114 B2 4/2020 Ercanbrack
10,646,746 B1 5/2020 Gomberg et al.
10,660,534 B2 5/2020 Lee et al.
10,678,890 B2 6/2020 Bitran et al.
10,685,092 B2 6/2020 Paparella et al.
10,741,285 B2 8/2020 Moturu
10,777,200 B2 9/2020 Will et al.
D899,605 S 10/2020 Ross et al.
10,792,495 B2 10/2020 Izvorski et al.
10,814,170 B2 10/2020 Wang et al.
10,857,426 B1 12/2020 Neumann
10,867,695 B2 12/2020 Neagle
10,874,905 B2 12/2020 Belson et al.
D907,143 S 1/2021 Ach et al.
10,881,911 B2 1/2021 Kwon et al.
10,902,944 B1 * 1/2021 Casey .................... A61B 34/25
10,918,332 B2 2/2021 Belson et al.
10,931,643 B1 2/2021 Neumann
10,987,176 B2 4/2021 Poltaretskyi et al.
10,991,463 B2 4/2021 Kutzko et al.
11,000,735 B2 5/2021 Orady et al.
11,045,709 B2 6/2021 Putnam
11,065,170 B2 7/2021 Yang et al.
11,065,527 B2 7/2021 Putnam
11,069,436 B2 7/2021 Mason et al.
11,071,597 B2 7/2021 Posnack et al.
11,075,000 B2 7/2021 Mason et al.
D928,635 S 8/2021 Hacking et al.
11,087,865 B2 8/2021 Mason et al.
11,094,400 B2 8/2021 Riley et al.
11,101,028 B2 8/2021 Mason et al.
11,107,591 B1 8/2021 Mason
11,139,060 B2 10/2021 Mason et al.
11,185,735 B2 11/2021 Arn et al.
11,185,738 B1 11/2021 McKirdy et al.
D939,096 S 12/2021 Lee
D939,644 S 12/2021 Ach et al.
D940,797 S 1/2022 Ach et al.
D940,891 S 1/2022 Lee
11,229,727 B2 1/2022 Tatonetti
11,229,788 B1 1/2022 John
11,265,234 B2 3/2022 Guaneri et al.
11,270,795 B2 3/2022 Mason et al.
11,272,879 B2 3/2022 Wiedenhoefer et al.
11,278,766 B2 3/2022 Lee
11,282,599 B2 3/2022 Mason et al.
11,282,604 B2 3/2022 Mason et al.
11,282,608 B2 3/2022 Mason et al.
11,284,797 B2 3/2022 Mason et al.
D948,639 S 4/2022 Ach et al.
11,295,848 B2 4/2022 Mason et al.
11,298,284 B2 4/2022 Bayerlein
11,309,085 B2 4/2022 Mason et al.
11,317,975 B2 5/2022 Mason et al.
11,325,005 B2 5/2022 Mason et al.
11,328,807 B2 5/2022 Mason et al.
11,337,648 B2 5/2022 Mason
11,347,829 B1 5/2022 Sclar et al.

(56) References Cited

U.S. PATENT DOCUMENTS 11,348,683 B2 5/2022 Guaneri et al.
11,370,328 B2 6/2022 Main
11,376,470 B2 7/2022 Weldemariam
11,404,150 B2 8/2022 Guaneri et al.
11,410,768 B2 8/2022 Mason et al.
11,422,841 B2 8/2022 Jeong
11,437,137 B1 9/2022 Harris
11,495,355 B2 11/2022 McNutt et al.
11,508,258 B2 11/2022 Nakashima et al.
11,508,482 B2 11/2022 Mason et al.
11,515,021 B2 11/2022 Mason
11,515,028 B2 11/2022 Mason
11,524,210 B2 12/2022 Kim et al.
11,527,326 B2 12/2022 McNair et al.
11,532,402 B2 12/2022 Farley et al.
11,534,654 B2 12/2022 Silcock et al.
D976,339 S 1/2023 Li
11,541,274 B2 1/2023 Hacking
11,553,969 B1 1/2023 Lang et al.
11,621,067 B1 4/2023 Nolan
11,636,944 B2 4/2023 Hanrahan et al.
11,654,327 B2 5/2023 Phillips et al.
11,663,673 B2 5/2023 Pyles
11,673,024 B2 6/2023 Omid-Zohoor
11,701,548 B2 7/2023 Posnack et al.
11,776,676 B2 10/2023 Savolainen
11,944,579 B2 4/2024 Sankai
11,957,960 B2 4/2024 Bissonnette et al.
12,004,871 B1 * 6/2024 Fazeli .................. A61B 5/0064
12,020,511 B1 6/2024 Denton et al.
12,057,210 B2 8/2024 Akinola et al.
12,205,704 B2 1/2025 Hosoi et al.
2001/0044573 A1 11/2001 Manoli
2002/0010596 A1 1/2002 Matory
2002/0072452 A1 6/2002 Torkelson
2002/0143279 A1 10/2002 Porter et al.
2002/0160883 A1 10/2002 Dugan
2002/0183599 A1 12/2002 Castellanos
2003/0013072 A1 1/2003 Thomas
2003/0036683 A1 2/2003 Kehr et al.
2003/0064860 A1 4/2003 Yamashita et al.
2003/0064863 A1 4/2003 Chen
2003/0083596 A1 5/2003 Kramer et al.
2003/0092536 A1 5/2003 Romanelli et al.
2003/0181832 A1 9/2003 Carnahan et al.
2004/0072652 A1 4/2004 Alessandri et al.
2004/0102931 A1 5/2004 Ellis et al.
2004/0106502 A1 6/2004 Sher
2004/0147969 A1 7/2004 Mann et al.
2004/0172093 A1 9/2004 Rummerfield
2004/0194572 A1 10/2004 Kim
2004/0197727 A1 10/2004 Sachdeva et al.
2004/0204959 A1 10/2004 Moreano et al.
2005/0015118 A1 1/2005 Davis et al.
2005/0020411 A1 1/2005 Andrews
2005/0043153 A1 2/2005 Krietzman
2005/0049122 A1 3/2005 Vallone et al.
2005/0085346 A1 4/2005 Johnson
2005/0085353 A1 4/2005 Johnson
2005/0115561 A1 6/2005 Stahmann
2005/0143641 A1 6/2005 Tashiro
2005/0274220 A1 12/2005 Reboullet
2006/0003871 A1 1/2006 Houghton et al.
2006/0046905 A1 3/2006 Doody, Jr. et al.
2006/0058648 A1 3/2006 Meier
2006/0064136 A1 3/2006 Wang
2006/0064329 A1 3/2006 Abolfathi et al.
2006/0129432 A1 6/2006 Choi et al.
2006/0199700 A1 9/2006 LaStayo et al.
2006/0247095 A1 11/2006 Rummerfield
2006/0277074 A1 12/2006 Einav
2007/0042868 A1 2/2007 Fisher et al.
2007/0118389 A1 5/2007 Shipon
2007/0118406 A1 5/2007 Killin et al.
2007/0137307 A1 6/2007 Gruben et al.
2007/0173392 A1 7/2007 Stanford
2007/0184414 A1 8/2007 Perez
2007/0194939 A1 8/2007 Alvarez et al.
2007/0219059 A1 9/2007 Schwartz
2007/0271065 A1 11/2007 Gupta et al.
2007/0287597 A1 12/2007 Cameron
2008/0021834 A1 1/2008 Holla et al.
2008/0077619 A1 3/2008 Gilley et al.
2008/0082356 A1 4/2008 Friedlander et al.
2008/0096726 A1 4/2008 Riley et al.
2008/0103023 A1 5/2008 Chung
2008/0153592 A1 6/2008 James-Herbert
2008/0161166 A1 7/2008 Lo
2008/0161733 A1 7/2008 Einav et al.
2008/0183500 A1 7/2008 Banigan
2008/0281633 A1 11/2008 Burdea et al.
2008/0300914 A1 12/2008 Karkanias et al.
2008/0312040 A1 12/2008 Ochi
2009/0011907 A1 1/2009 Radow et al.
2009/0037334 A1 2/2009 Hsu
2009/0058635 A1 3/2009 LaLonde et al.
2009/0070138 A1 3/2009 Langheier et al.
2009/0157617 A1 6/2009 Herlocker
2009/0211395 A1 8/2009 Mule
2009/0270227 A1 10/2009 Ashby et al.
2009/0287503 A1 11/2009 Angell et al.
2009/0299766 A1 12/2009 Friedlander et al.
2010/0048358 A1 2/2010 Tchao et al.
2010/0062818 A1 3/2010 Haughay, Jr.
2010/0076786 A1 3/2010 Dalton et al.
2010/0121160 A1 5/2010 Stark et al.
2010/0173747 A1 7/2010 Chen et al.
2010/0216168 A1 8/2010 Heinzman et al.
2010/0234184 A1 9/2010 Le Page et al.
2010/0248899 A1 9/2010 Bedell et al.
2010/0248905 A1 9/2010 Lu
2010/0262052 A1 10/2010 Lunau et al.
2010/0268304 A1 10/2010 Matos
2010/0293003 A1 * 11/2010 Abbo ................ G06F 16/90328
707/706
2010/0298102 A1 11/2010 Bosecker et al.
2010/0326207 A1 12/2010 Topel
2010/0332583 A1 12/2010 Szabo
2011/0010188 A1 1/2011 Yoshikawa et al.
2011/0047108 A1 2/2011 Chakrabarty et al.
2011/0082007 A1 4/2011 Birrell
2011/0087137 A1 4/2011 Hanoun
2011/0119212 A1 5/2011 De Bruin et al.
2011/0172059 A1 7/2011 Watterson et al.
2011/0195819 A1 8/2011 Shaw et al.
2011/0218462 A1 9/2011 Smith
2011/0218814 A1 9/2011 Coats
2011/0275483 A1 11/2011 Dugan
2011/0281249 A1 11/2011 Gammell et al.
2011/0306846 A1 12/2011 Osorio
2012/0041771 A1 2/2012 Cosentino et al.
2012/0065987 A1 3/2012 Farooq et al.
2012/0116258 A1 5/2012 Lee
2012/0130196 A1 5/2012 Jain et al.
2012/0130197 A1 5/2012 Kugler et al.
2012/0167709 A1 7/2012 Chen et al.
2012/0183939 A1 7/2012 Aragones et al.
2012/0190502 A1 7/2012 Paulus et al.
2012/0232438 A1 9/2012 Cataldi et al.
2012/0253241 A1 10/2012 Levital
2012/0259648 A1 10/2012 Mallon et al.
2012/0259649 A1 10/2012 Mallon et al.
2012/0278759 A1 11/2012 Curl et al.
2012/0295240 A1 11/2012 Walker et al.
2012/0296455 A1 11/2012 Ohnemus et al.
2012/0310667 A1 12/2012 Altman et al.
2013/0066647 A1 3/2013 Andrie
2013/0079925 A1 3/2013 Alaklabi et al.
2013/0083054 A1 4/2013 Bayouk
2013/0108594 A1 5/2013 Martin-Rendon et al.
2013/0110545 A1 5/2013 Smallwood
2013/0123071 A1 5/2013 Rhea
2013/0123667 A1 5/2013 Komatireddy et al.
2013/0137550 A1 5/2013 Skinner et al.

(56) References Cited

U.S. PATENT DOCUMENTS

2013/0137552 A1 5/2013 Kemp et al.
2013/0158368 A1 6/2013 Pacione
2013/0165195 A1* 6/2013 Watterson .......... A63B 24/0084 463/6
2013/0178334 A1 7/2013 Brammer
2013/0211281 A1 8/2013 Ross et al.
2013/0211774 A1 8/2013 Bentley
2013/0253943 A1 9/2013 Lee et al.
2013/0274069 A1 10/2013 Watterson et al.
2013/0296987 A1 11/2013 Rogers et al.
2013/0318027 A1 11/2013 Almogy et al.
2013/0332616 A1 12/2013 Landwehr
2013/0345025 A1 12/2013 van der Merwe
2014/0006042 A1 1/2014 Keefe et al.
2014/0011640 A1 1/2014 Dugan
2014/0031174 A1 1/2014 Huang
2014/0038781 A1 2/2014 Foley et al.
2014/0062900 A1 3/2014 Kaula et al.
2014/0074179 A1 3/2014 Heldman et al.
2014/0089836 A1 3/2014 Damani et al.
2014/0108035 A1 4/2014 Akbay
2014/0113261 A1 4/2014 Akiba
2014/0113768 A1 4/2014 Lin et al.
2014/0135173 A1 5/2014 Watterson
2014/0149129 A1 5/2014 Getchius
2014/0155129 A1 6/2014 Dugan
2014/0163439 A1 6/2014 Uryash et al.
2014/0172442 A1 6/2014 Broderick
2014/0172460 A1 6/2014 Kohli
2014/0172514 A1 6/2014 Schumann et al.
2014/0188009 A1 7/2014 Lange et al.
2014/0194250 A1 7/2014 Reich et al.
2014/0194251 A1 7/2014 Reich et al.
2014/0200414 A1 7/2014 Osorio
2014/0207264 A1 7/2014 Quy
2014/0207486 A1 7/2014 Carty et al.
2014/0228649 A1 8/2014 Rayner et al.
2014/0246499 A1 9/2014 Proud et al.
2014/0256511 A1 9/2014 Smith
2014/0257837 A1 9/2014 Walker et al.
2014/0274565 A1 9/2014 Boyette et al.
2014/0274622 A1 9/2014 Leonhard
2014/0275816 A1 9/2014 Sandmore
2014/0303540 A1 10/2014 Baym
2014/0309083 A1 10/2014 Dugan
2014/0322686 A1 10/2014 Kang
2014/0347265 A1 11/2014 Aimone et al.
2014/0371816 A1 12/2014 Matos
2014/0372133 A1 12/2014 Austrum et al.
2015/0025816 A1 1/2015 Ross
2015/0045700 A1 2/2015 Cavanagh et al.
2015/0046192 A1 2/2015 Raduchel
2015/0051721 A1 2/2015 Cheng
2015/0065213 A1 3/2015 Dugan
2015/0073814 A1 3/2015 Linebaugh
2015/0088544 A1 3/2015 Goldberg
2015/0094192 A1 4/2015 Skwortsow et al.
2015/0099458 A1 4/2015 Weisner et al.
2015/0099952 A1 4/2015 Lain et al.
2015/0111644 A1 4/2015 Larson
2015/0112230 A1 4/2015 Iglesias
2015/0112702 A1 4/2015 Joao et al.
2015/0130830 A1 5/2015 Nagasaki
2015/0141200 A1 5/2015 Murray et al.
2015/0142142 A1 5/2015 Campana Aguilera et al.
2015/0149217 A1 5/2015 Kaburagi
2015/0151162 A1 6/2015 Dugan
2015/0157938 A1 6/2015 Domansky et al.
2015/0161331 A1 6/2015 Oleynik
2015/0161876 A1 6/2015 Castillo
2015/0174446 A1 6/2015 Chiang
2015/0196804 A1 7/2015 Koduri
2015/0196805 A1 7/2015 Koduri
2015/0199494 A1* 7/2015 Koduri .................. G16H 20/30 700/91
2015/0217056 A1 8/2015 Kadavy et al.
2015/0251074 A1 9/2015 Ahmed et al.
2015/0257679 A1 9/2015 Ross
2015/0265209 A1 9/2015 Zhang
2015/0290061 A1 10/2015 Stafford et al.
2015/0331997 A1 11/2015 Joao
2015/0335950 A1* 11/2015 Eder .................. A63B 22/0605 482/8
2015/0335951 A1 11/2015 Eder
2015/0339442 A1 11/2015 Oleynik
2015/0341812 A1 11/2015 Dion et al.
2015/0351664 A1 12/2015 Ross
2015/0351665 A1 12/2015 Ross
2015/0360069 A1 12/2015 Marti et al.
2015/0379232 A1 12/2015 Mainwaring et al.
2015/0379430 A1 12/2015 Dirac et al.
2016/0004820 A1 1/2016 Moore
2016/0007885 A1 1/2016 Basta
2016/0015995 A1 1/2016 Leung et al.
2016/0023081 A1 1/2016 Popa-Simil et al.
2016/0045170 A1 2/2016 Migita
2016/0081594 A1 3/2016 Gaddipati
2016/0086500 A1* 3/2016 Kaleal, III ............... A61B 5/20 434/257
2016/0096073 A1 4/2016 Rahman et al.
2016/0117471 A1 4/2016 Belt et al.
2016/0132643 A1 5/2016 Radhakrishna et al.
2016/0140319 A1 5/2016 Stark
2016/0143593 A1 5/2016 Fu et al.
2016/0151670 A1 6/2016 Dugan
2016/0158534 A1 6/2016 Guarraia et al.
2016/0166833 A1 6/2016 Bum
2016/0166881 A1 6/2016 Ridgel et al.
2016/0193306 A1 7/2016 Rabovsky et al.
2016/0197918 A1 7/2016 Turgeman et al.
2016/0213924 A1 7/2016 Coleman
2016/0250519 A1 9/2016 Watterson
2016/0275259 A1 9/2016 Nolan et al.
2016/0287166 A1 10/2016 Tran
2016/0294837 A1 10/2016 Turgeman
2016/0302666 A1 10/2016 Shaya
2016/0302721 A1 10/2016 Wiedenhoefer et al.
2016/0317869 A1 11/2016 Dugan
2016/0322078 A1 11/2016 Bose et al.
2016/0325140 A1 11/2016 Wu
2016/0332028 A1 11/2016 Melnik
2016/0345841 A1 12/2016 Jang et al.
2016/0354636 A1 12/2016 Jang
2016/0361025 A1 12/2016 Reicher et al.
2016/0361597 A1 12/2016 Cole et al.
2016/0373477 A1 12/2016 Moyle
2017/0000422 A1 1/2017 Moturu et al.
2017/0004260 A1 1/2017 Moturu et al.
2017/0011179 A1 1/2017 Arshad et al.
2017/0017760 A1 1/2017 Freese et al.
2017/0032092 A1 2/2017 Mink et al.
2017/0033375 A1 2/2017 Ohmori et al.
2017/0042467 A1 2/2017 Herr et al.
2017/0043160 A1 2/2017 Goodall et al.
2017/0046488 A1 2/2017 Pereira
2017/0065851 A1 3/2017 Deluca et al.
2017/0069223 A1 3/2017 Cramer et al.
2017/0080320 A1 3/2017 Smith
2017/0091422 A1 3/2017 Kumar et al.
2017/0095670 A1 4/2017 Ghaffari et al.
2017/0095692 A1 4/2017 Chang et al.
2017/0095693 A1 4/2017 Chang et al.
2017/0100637 A1 4/2017 Princen et al.
2017/0106242 A1 4/2017 Dugan
2017/0113092 A1 4/2017 Johnson
2017/0128769 A1 5/2017 Long et al.
2017/0132947 A1 5/2017 Maeda et al.
2017/0136296 A1 5/2017 Barrera et al.
2017/0136298 A1 5/2017 Bae
2017/0143261 A1 5/2017 Wiedenhoefer et al.
2017/0147752 A1 5/2017 Toru
2017/0147789 A1 5/2017 Wiedenhoefer et al.
2017/0148297 A1 5/2017 Ross
2017/0168555 A1 6/2017 Munoz et al.

(56) References Cited

U.S. PATENT DOCUMENTS

2017/0169177 A1 6/2017 Beale
2017/0173391 A1 6/2017 Wiebe
2017/0181698 A1 6/2017 Wiedenhoefer et al.
2017/0190052 A1 7/2017 Jaekel et al.
2017/0202724 A1 7/2017 De Rossi
2017/0209766 A1 7/2017 Riley et al.
2017/0220751 A1 8/2017 Davis
2017/0228517 A1 8/2017 Saliman et al.
2017/0235882 A1 8/2017 Orlov et al.
2017/0235906 A1 8/2017 Dorris et al.
2017/0243028 A1 8/2017 LaFever et al.
2017/0258370 A1 9/2017 Plotnik-Peleg et al.
2017/0262604 A1* 9/2017 Francois ................ G16H 10/60
2017/0265800 A1 9/2017 Auchinleck et al.
2017/0266501 A1 9/2017 Sanders et al.
2017/0270260 A1 9/2017 Shetty
2017/0277841 A1 9/2017 Shankar et al.
2017/0278209 A1 9/2017 Olsen et al.
2017/0282015 A1 10/2017 Wicks et al.
2017/0283508 A1 10/2017 Demopulos et al.
2017/0286621 A1 10/2017 Cox
2017/0291067 A1 10/2017 Jang et al.
2017/0296861 A1 10/2017 Burkinshaw
2017/0300654 A1 10/2017 Stein et al.
2017/0304024 A1 10/2017 Nobrega
2017/0312614 A1 11/2017 Tran et al.
2017/0323481 A1 11/2017 Tran et al.
2017/0329917 A1 11/2017 McRaith et al.
2017/0329933 A1 11/2017 Brust
2017/0333755 A1 11/2017 Rider
2017/0337033 A1 11/2017 Duyan et al.
2017/0337334 A1 11/2017 Stanczak
2017/0344726 A1 11/2017 Duffy et al.
2017/0347923 A1 12/2017 Roh
2017/0352157 A1 12/2017 Madabhushi
2017/0360586 A1 12/2017 Dempers et al.
2017/0361165 A1 12/2017 Miller et al.
2017/0367606 A1 12/2017 Lee
2017/0368413 A1 12/2017 Shavit
2018/0017806 A1 1/2018 Wang et al.
2018/0028896 A1 2/2018 Ray
2018/0036591 A1 2/2018 King et al.
2018/0036593 A1 2/2018 Ridgel et al.
2018/0052962 A1 2/2018 Van Der Koijk et al.
2018/0052968 A1 2/2018 Hickle et al.
2018/0056104 A1 3/2018 Cromie et al.
2018/0056130 A1 3/2018 Bitran et al.
2018/0060494 A1 3/2018 Dias et al.
2018/0070864 A1 3/2018 Schuster
2018/0071565 A1 3/2018 Gomberg et al.
2018/0071566 A1 3/2018 Gomberg et al.
2018/0071569 A1 3/2018 Gomberg et al.
2018/0071570 A1 3/2018 Gomberg et al.
2018/0071571 A1 3/2018 Gomberg et al.
2018/0071572 A1 3/2018 Gomberg et al.
2018/0071583 A1 3/2018 Paiz
2018/0075205 A1 3/2018 Moturu et al.
2018/0078149 A1 3/2018 Fonte et al.
2018/0078182 A1 3/2018 Chen
2018/0078843 A1 3/2018 Tran et al.
2018/0085615 A1 3/2018 Astolfi et al.
2018/0085630 A1 3/2018 Capell
2018/0089385 A1 3/2018 Gupta
2018/0096111 A1 4/2018 Wells et al.
2018/0099178 A1 4/2018 Schaefer et al.
2018/0102190 A1 4/2018 Hogue et al.
2018/0103859 A1 4/2018 Provenzano
2018/0113985 A1 4/2018 Gandy et al.
2018/0116741 A1 5/2018 Garcia Kilroy et al.
2018/0117417 A1 5/2018 Davis
2018/0130555 A1 5/2018 Chronis et al.
2018/0133551 A1* 5/2018 Chang ................ A63B 24/0075
2018/0140927 A1 5/2018 Kito
2018/0146870 A1 5/2018 Shemesh
2018/0177612 A1 6/2018 Trabish et al.
2018/0178061 A1 6/2018 O'Larte et al.
2018/0199855 A1 7/2018 Odame et al.
2018/0200577 A1 7/2018 Dugan
2018/0214729 A1 8/2018 Rubin
2018/0220935 A1 8/2018 Tadano et al.
2018/0228682 A1 8/2018 Bayerlein et al.
2018/0232492 A1* 8/2018 Al-Alul .................. G16H 20/30
2018/0236307 A1 8/2018 Hyde et al.
2018/0240552 A1 8/2018 Tuyl et al.
2018/0253991 A1 9/2018 Tang et al.
2018/0255110 A1 9/2018 Dowlatkhah et al.
2018/0256079 A1 9/2018 Yang et al.
2018/0256939 A1 9/2018 Malcolm
2018/0263530 A1 9/2018 Jung
2018/0263535 A1 9/2018 Cramer
2018/0263552 A1 9/2018 Graman et al.
2018/0264312 A1 9/2018 Pompile et al.
2018/0271432 A1 9/2018 Auchinleck et al.
2018/0272184 A1 9/2018 Vassilaros et al.
2018/0280784 A1 10/2018 Romeo et al.
2018/0285463 A1 10/2018 Choi et al.
2018/0290017 A1 10/2018 Fung
2018/0296143 A1 10/2018 Anderson et al.
2018/0296157 A1 10/2018 Bleich et al.
2018/0318122 A1 11/2018 LeCursi et al.
2018/0326243 A1 11/2018 Badi et al.
2018/0330058 A1 11/2018 Bates
2018/0330810 A1 11/2018 Gamarnik
2018/0330824 A1 11/2018 Athey et al.
2018/0353812 A1* 12/2018 Lannon .................. G16H 20/30
2018/0360340 A1 12/2018 Rehse et al.
2018/0361203 A1* 12/2018 Wang ..................... G06N 20/00
2018/0366225 A1 12/2018 Mansi et al.
2018/0373844 A1 12/2018 Ferrandez-Escamez et al.
2019/0005195 A1 1/2019 Peterson
2019/0009135 A1 1/2019 Wu
2019/0019163 A1 1/2019 Batey et al.
2019/0019573 A1 1/2019 Lake et al.
2019/0019578 A1 1/2019 Vaccaro
2019/0021929 A1* 1/2019 Einav ............... A63B 21/00181
2019/0030415 A1 1/2019 Volpe, Jr.
2019/0031284 A1 1/2019 Fuchs
2019/0046794 A1 2/2019 Goodall et al.
2019/0060708 A1 2/2019 Fung
2019/0065970 A1 2/2019 Bonutti et al.
2019/0066832 A1 2/2019 Kang et al.
2019/0076701 A1 3/2019 Dugan
2019/0080802 A1 3/2019 Ziobro et al.
2019/0083846 A1 3/2019 Eder
2019/0088356 A1 3/2019 Oliver et al.
2019/0090744 A1 3/2019 Mahfouz
2019/0096534 A1 3/2019 Joao
2019/0105551 A1 4/2019 Ray
2019/0108912 A1 4/2019 Spurlock, III
2019/0111299 A1 4/2019 Radcliffe et al.
2019/0115097 A1 4/2019 Macoviak et al.
2019/0117156 A1 4/2019 Howard et al.
2019/0118038 A1 4/2019 Tana et al.
2019/0118066 A1 4/2019 Cardona
2019/0126099 A1 5/2019 Hoang
2019/0132948 A1 5/2019 Longinotti-Buitoni et al.
2019/0134454 A1 5/2019 Mahoney et al.
2019/0137988 A1 5/2019 Cella et al.
2019/0143191 A1 5/2019 Ran et al.
2019/0143193 A1 5/2019 Kim
2019/0145774 A1 5/2019 Ellis
2019/0163876 A1 5/2019 Remme et al.
2019/0167988 A1 6/2019 Shahriari et al.
2019/0172587 A1 6/2019 Park et al.
2019/0175988 A1 6/2019 Volterrani et al.
2019/0183715 A1 6/2019 Kapure et al.
2019/0200920 A1 7/2019 Tien et al.
2019/0209891 A1 7/2019 Fung
2019/0214119 A1 7/2019 Wachira et al.
2019/0223797 A1 7/2019 Tran
2019/0224528 A1 7/2019 Omid-Zohoor et al.
2019/0228856 A1 7/2019 Leifer
2019/0232108 A1 8/2019 Kovach et al.
2019/0240103 A1 8/2019 Hepler et al.

(56) References Cited

U.S. PATENT DOCUMENTS

2019/0240541 A1 8/2019 Denton et al.
2019/0244540 A1 8/2019 Errante et al.
2019/0247718 A1 8/2019 Blevins
2019/0251456 A1 8/2019 Constantin
2019/0251723 A1 8/2019 Coppersmith
2019/0261959 A1 8/2019 Frankel
2019/0262084 A1 8/2019 Roh
2019/0269343 A1 9/2019 Ramos Murguialday et al.
2019/0274523 A1 9/2019 Bates et al.
2019/0275368 A1 9/2019 Maroldi
2019/0283247 A1 9/2019 Chang
2019/0290191 A1 9/2019 Leppäluoto et al.
2019/0304584 A1 10/2019 Savolainen
2019/0307983 A1 10/2019 Goldman
2019/0314681 A1 10/2019 Yang
2019/0344123 A1 11/2019 Rubin et al.
2019/0354632 A1 11/2019 Mital et al.
2019/0362242 A1 11/2019 Pillai et al.
2019/0366146 A1 12/2019 Tong et al.
2019/0371472 A1 12/2019 Blanchard
2019/0385199 A1 12/2019 Bender et al.
2019/0388728 A1 12/2019 Wang et al.
2019/0392936 A1 12/2019 Arric et al.
2019/0392939 A1 12/2019 Basta et al.
2020/0005928 A1 1/2020 Daniel
2020/0015736 A1 1/2020 Alhathal
2020/0034665 A1 1/2020 Ghanta
2020/0034707 A1 1/2020 Kivatinos et al.
2020/0038703 A1 2/2020 Cleary et al.
2020/0051446 A1 2/2020 Rubinstein
2020/0054922 A1 2/2020 Azaria
2020/0066390 A1 2/2020 Svendrys et al.
2020/0085300 A1 3/2020 Kwatra et al.
2020/0090802 A1 3/2020 Maron
2020/0093418 A1 3/2020 Kluger et al.
2020/0098463 A1 3/2020 Arunachalam et al.
2020/0121987 A1 4/2020 Loh
2020/0129237 A1 4/2020 Erdem
2020/0129808 A1 4/2020 Fomin
2020/0139194 A1 5/2020 Min
2020/0143922 A1 5/2020 Chekroud et al.
2020/0151595 A1* 5/2020 Jayalath ............. A63B 21/0442
2020/0151646 A1 5/2020 De La Fuente Sanchez
2020/0152339 A1 5/2020 Pulitzer et al.
2020/0160198 A1 5/2020 Reeves et al.
2020/0170876 A1 6/2020 Kapure et al.
2020/0176098 A1 6/2020 Lucas et al.
2020/0188774 A1 6/2020 Fung
2020/0197744 A1 6/2020 Schweighofer
2020/0221975 A1 7/2020 Basta et al.
2020/0237291 A1* 7/2020 Sundaram ............ A61B 5/4528
2020/0237452 A1 7/2020 Wolf et al.
2020/0261763 A1 8/2020 Park
2020/0267487 A1 8/2020 Siva
2020/0275886 A1 9/2020 Mason
2020/0289045 A1 9/2020 Hacking et al.
2020/0289046 A1 9/2020 Hacking et al.
2020/0289879 A1 9/2020 Hacking et al.
2020/0289880 A1 9/2020 Hacking et al.
2020/0289881 A1 9/2020 Hacking et al.
2020/0289889 A1 9/2020 Hacking et al.
2020/0293712 A1 9/2020 Potts et al.
2020/0303063 A1 9/2020 Sharma et al.
2020/0312447 A1 10/2020 Bohn et al.
2020/0320454 A1 10/2020 Almashor
2020/0334972 A1 10/2020 Gopalakrishnan
2020/0338394 A1 10/2020 Neumann
2020/0346072 A1* 11/2020 Shah .................. G09B 19/0038
2020/0353314 A1 11/2020 Messinger
2020/0357299 A1 11/2020 Patel et al.
2020/0365256 A1 11/2020 Hayashitani et al.
2020/0376327 A1 12/2020 Bissonnette
2020/0391080 A1 12/2020 Powers
2020/0395112 A1 12/2020 Ronner
2020/0398083 A1 12/2020 Adelsheim
2020/0401224 A1 12/2020 Cotton
2020/0402638 A1 12/2020 Song et al.
2020/0402662 A1 12/2020 Esmailian et al.
2020/0410374 A1 12/2020 White
2020/0410385 A1 12/2020 Otsuki
2020/0410893 A1 12/2020 Ridington
2020/0411162 A1 12/2020 Lien et al.
2020/0411170 A1 12/2020 Brown
2021/0005224 A1 1/2021 Rothschild et al.
2021/0005319 A1 1/2021 Otsuki et al.
2021/0008413 A1 1/2021 Asikainen et al.
2021/0015560 A1 1/2021 Boddington et al.
2021/0027889 A1 1/2021 Neil et al.
2021/0035674 A1 2/2021 Volosin et al.
2021/0050086 A1 2/2021 Rose et al.
2021/0065855 A1 3/2021 Pepin et al.
2021/0074178 A1 3/2021 Ilan et al.
2021/0076981 A1 3/2021 Hacking et al.
2021/0077860 A1 3/2021 Posnack et al.
2021/0077884 A1 3/2021 De Las Casas Zolezzi et al.
2021/0082554 A1 3/2021 Kalia et al.
2021/0093891 A1 4/2021 Sheng
2021/0098099 A1 4/2021 Neumann
2021/0098129 A1 4/2021 Neumann
2021/0101051 A1 4/2021 Posnack et al.
2021/0106899 A1 4/2021 Willardson
2021/0113890 A1 4/2021 Posnack et al.
2021/0125696 A1 4/2021 Liu et al.
2021/0127974 A1 5/2021 Mason et al.
2021/0128080 A1 5/2021 Mason et al.
2021/0128255 A1 5/2021 Mason et al.
2021/0128978 A1 5/2021 Gilstrom et al.
2021/0134412 A1 5/2021 Guaneri et al.
2021/0134425 A1 5/2021 Mason et al.
2021/0134427 A1 5/2021 Mason et al.
2021/0134428 A1 5/2021 Mason et al.
2021/0134429 A1* 5/2021 Mason .................. G16H 40/67
2021/0134430 A1 5/2021 Mason et al.
2021/0134432 A1 5/2021 Mason et al.
2021/0134456 A1 5/2021 Posnack et al.
2021/0134457 A1 5/2021 Mason et al.
2021/0134458 A1 5/2021 Mason et al.
2021/0134463 A1 5/2021 Mason et al.
2021/0138304 A1 5/2021 Mason et al.
2021/0142875 A1 5/2021 Mason et al.
2021/0142893 A1 5/2021 Guaneri et al.
2021/0142898 A1 5/2021 Mason et al.
2021/0142903 A1 5/2021 Mason et al.
2021/0144074 A1 5/2021 Guaneri et al.
2021/0186419 A1 6/2021 Van Ee et al.
2021/0187348 A1 6/2021 Phillips et al.
2021/0202090 A1 7/2021 ODonovan et al.
2021/0202103 A1 7/2021 Bostic et al.
2021/0205660 A1 7/2021 Shavit
2021/0217516 A1* 7/2021 Nash ...................... G16H 50/30
2021/0236020 A1 8/2021 Matijevich et al.
2021/0240853 A1 8/2021 Carlson
2021/0241137 A1 8/2021 Jain et al.
2021/0244998 A1 8/2021 Hacking et al.
2021/0245003 A1 8/2021 Turner
2021/0251562 A1 8/2021 Jain
2021/0272677 A1 9/2021 Barbee
2021/0291010 A1 9/2021 Miller
2021/0338469 A1 11/2021 Dempers
2021/0343384 A1 11/2021 Purushothaman et al.
2021/0345879 A1 11/2021 Mason et al.
2021/0345975 A1 11/2021 Mason et al.
2021/0350888 A1 11/2021 Guaneri et al.
2021/0350898 A1 11/2021 Mason et al.
2021/0350899 A1 11/2021 Mason et al.
2021/0350901 A1 11/2021 Mason et al.
2021/0350902 A1 11/2021 Mason et al.
2021/0350914 A1 11/2021 Guaneri et al.
2021/0350926 A1 11/2021 Mason et al.
2021/0354002 A1 11/2021 Schaefer
2021/0361514 A1 11/2021 Choi et al.
2021/0366587 A1 11/2021 Mason et al.
2021/0375425 A1 12/2021 Zhang
2021/0383909 A1 12/2021 Mason et al.

(56) References Cited

U.S. PATENT DOCUMENTS

2021/0391091 A1 12/2021 Mason
2021/0394011 A1 12/2021 Neuhaus et al.
2021/0398668 A1 12/2021 Chock et al.
2021/0406738 A1 12/2021 O'Donncha et al.
2021/0407670 A1 12/2021 Mason et al.
2021/0407681 A1 12/2021 Mason et al.
2022/0000556 A1 1/2022 Casey et al.
2022/0015838 A1 1/2022 Posnack et al.
2022/0016480 A1 1/2022 Bissonnette et al.
2022/0016482 A1 1/2022 Bissonnette
2022/0016484 A1 1/2022 Bissonnett et al.
2022/0016485 A1 1/2022 Bissonnette et al.
2022/0016486 A1 1/2022 Bissonnette et al.
2022/0020469 A1 1/2022 Tanner
2022/0044806 A1 2/2022 Sanders et al.
2022/0047921 A1 2/2022 Bissonnette et al.
2022/0066548 A1 3/2022 Helot
2022/0079690 A1 3/2022 Mason et al.
2022/0080256 A1 3/2022 Arn et al.
2022/0080265 A1 3/2022 Watterson
2022/0096006 A1 3/2022 Wu et al.
2022/0105384 A1 4/2022 Hacking et al.
2022/0105385 A1 4/2022 Hacking et al.
2022/0105390 A1 4/2022 Yuasa
2022/0115133 A1 4/2022 Mason et al.
2022/0117514 A1 4/2022 Kuhn et al.
2022/0118218 A1 4/2022 Bense et al.
2022/0122724 A1 4/2022 Durlach et al.
2022/0126169 A1 4/2022 Mason
2022/0133576 A1 5/2022 Choi et al.
2022/0148725 A1 5/2022 Mason et al.
2022/0158916 A1 5/2022 Mason et al.
2022/0165398 A1 5/2022 Avila-Hernandez et al.
2022/0176039 A1 6/2022 Lintereur et al.
2022/0181004 A1 6/2022 Zilca et al.
2022/0193491 A1 6/2022 Mason et al.
2022/0230729 A1 7/2022 Mason
2022/0238222 A1 7/2022 Neuberg
2022/0238223 A1 7/2022 Mason et al.
2022/0258935 A1 8/2022 Kraft
2022/0262483 A1 8/2022 Rosenberg et al.
2022/0262504 A1 8/2022 Bratty et al.
2022/0266094 A1 8/2022 Mason et al.
2022/0270738 A1 8/2022 Mason et al.
2022/0273985 A1 9/2022 Jeong et al.
2022/0273986 A1 9/2022 Mason
2022/0288460 A1 9/2022 Mason
2022/0288461 A1 9/2022 Ashley et al.
2022/0288462 A1 9/2022 Ashley et al.
2022/0293257 A1 9/2022 Guaneri et al.
2022/0300787 A1 9/2022 Wall et al.
2022/0304881 A1 9/2022 Choi et al.
2022/0304882 A1 9/2022 Choi
2022/0305291 A1 9/2022 Hibbard
2022/0305328 A1 9/2022 Choi et al.
2022/0314072 A1 10/2022 Bissonnette et al.
2022/0314075 A1 10/2022 Mason et al.
2022/0323826 A1 10/2022 Khurana
2022/0327714 A1 10/2022 Cook et al.
2022/0327807 A1 10/2022 Cook et al.
2022/0328181 A1 10/2022 Mason et al.
2022/0330823 A1 10/2022 Janssen
2022/0331663 A1 10/2022 Mason
2022/0336077 A1 10/2022 Chen et al.
2022/0338761 A1 10/2022 Maddahi et al.
2022/0339052 A1 10/2022 Kim
2022/0339501 A1 10/2022 Mason et al.
2022/0342969 A1 10/2022 Watterson et al.
2022/0346703 A1 11/2022 Abdo et al.
2022/0370851 A1 11/2022 Guidarelli et al.
2022/0384010 A1 12/2022 Kanayama
2022/0384012 A1 12/2022 Mason
2022/0392591 A1 12/2022 Guaneri et al.
2022/0395232 A1 12/2022 Locke
2022/0401783 A1 12/2022 Choi
2022/0415469 A1 12/2022 Mason
2022/0415471 A1 12/2022 Mason
2023/0001268 A1 1/2023 Bissonnette et al.
2023/0013530 A1 1/2023 Mason
2023/0014598 A1 1/2023 Mason et al.
2023/0029639 A1 2/2023 Roy
2023/0047253 A1 2/2023 Gnanasambandam et al.
2023/0048040 A1 2/2023 Hacking et al.
2023/0051751 A1 2/2023 Hacking et al.
2023/0055078 A1 2/2023 Malcolm
2023/0058605 A1 2/2023 Mason
2023/0060039 A1 2/2023 Mason
2023/0072368 A1 3/2023 Mason
2023/0078793 A1 3/2023 Mason
2023/0119461 A1 4/2023 Mason
2023/0190100 A1 6/2023 Stump
2023/0197240 A1 6/2023 Rosenberg
2023/0201656 A1 6/2023 Hacking et al.
2023/0207097 A1 6/2023 Mason
2023/0207124 A1 6/2023 Walsh et al.
2023/0215539 A1 7/2023 Rosenberg et al.
2023/0215552 A1 7/2023 Khotilovich et al.
2023/0218950 A1 7/2023 Belson et al.
2023/0245747 A1 8/2023 Rosenberg et al.
2023/0245748 A1 8/2023 Rosenberg et al.
2023/0245750 A1 8/2023 Rosenberg et al.
2023/0245751 A1 8/2023 Rosenberg et al.
2023/0249599 A1 8/2023 Nicola
2023/0253089 A1 8/2023 Rosenberg et al.
2023/0255555 A1 8/2023 Sundaram et al.
2023/0263428 A1 8/2023 Hull et al.
2023/0274813 A1 8/2023 Rosenberg et al.
2023/0282329 A1 9/2023 Mason et al.
2023/0364471 A1 11/2023 Choi et al.
2023/0364472 A1 11/2023 Posnack
2023/0368886 A1 11/2023 Rosenberg
2023/0377710 A1 11/2023 Chen et al.
2023/0377711 A1 11/2023 Rosenberg
2023/0377712 A1 11/2023 Rosenberg
2023/0386639 A1 11/2023 Rosenberg
2023/0390627 A1 12/2023 Bolton
2023/0395231 A1 12/2023 Rosenberg
2023/0395232 A1 12/2023 Rosenberg
2024/0029856 A1 1/2024 Rosenberg
2024/0058651 A1 2/2024 Bissonnette
2024/0177846 A1 5/2024 Gnanasambandam
2024/0203580 A1 6/2024 Mason

FOREIGN PATENT DOCUMENTS

CN 101964151 A 2/2011
CN 201889024 U 7/2011
CN 202220794 U 5/2012
CN 102670381 A 9/2012
CN 103263336 A 8/2013
CN 103390357 A 11/2013
CN 103473631 A 12/2013
CN 103488880 A 1/2014
CN 103501328 A 1/2014
CN 103721343 A 4/2014
CN 203677851 U 7/2014
CN 104335211 A 2/2015
CN 105263448 A 1/2016
CN 105620643 A 6/2016
CN 105683977 A 6/2016
CN 103136447 B 8/2016
CN 105894088 A 8/2016
CN 105930668 A 9/2016
CN 205626871 U 10/2016
CN 106127646 A 11/2016
CN 106236502 A 12/2016
CN 106510985 A 3/2017
CN 106621195 A 5/2017
CN 107066819 A 8/2017
CN 107430641 A 12/2017
CN 107551475 A 1/2018
CN 107736982 A 2/2018
CN 107930021 A 4/2018
CN 108078737 A 5/2018

(56) References Cited

FOREIGN PATENT DOCUMENTS

| | | | |
|---|---|---|---|
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |

(56) References Cited

FOREIGN PATENT DOCUMENTS

| | | | |
|---|---|---|---|
| KR | 102246051 | B1 | 4/2021 |
| KR | 102246052 | B1 | 4/2021 |
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| RU | 2014131288 | A | 2/2016 |
| RU | 2607953 | C2 | 1/2017 |
| TW | M474545 | U | 3/2014 |
| TW | I442956 | B | 7/2014 |
| TW | M638437 | U | 3/2023 |
| WO | 1998009687 | A1 | 3/1998 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | A1 | 5/2003 |
| WO | 2005018453 | A1 | 3/2005 |
| WO | 2005074369 | A2 | 8/2005 |
| WO | 2006004430 | A2 | 1/2006 |
| WO | 2006012694 | A1 | 2/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019106003 | A1 | 6/2019 |
| WO | 2019143940 | A1 | 7/2019 |
| WO | 2020014710 | A2 | 1/2020 |
| WO | 2020075190 | A1 | 4/2020 |
| WO | 2020130979 | A1 | 6/2020 |
| WO | 2020149815 | A2 | 7/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Davenport et al., "The Potential For Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Jeong et al., "Computer-assisted upper extremity training using interactive biking exercise (iBikE) platform," Sep. 2012, pp. 1-5, 34th Annual International Conference of the IEEE EMBS.

(56) References Cited

OTHER PUBLICATIONS

Jeong et al., "Remotely controlled biking is associated with improved adherence to prescribed cycling speed," Technology and Health Care 23, 2015, 7 pages.
Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.
Blasiak et al., "CURATE.AI: Optimizing Personalized Medicine with Artificial Intelligence," SLAS TECHNOLOGY: Translating Life Sciences Innovation, 2020, 11 pages.
Gerbild et al., "Physical Activity to Improve Erectile Dysfunction: A Systematic Review of Intervention Studies," Sexual Medicine, 2018, 15 pages.
Ahmed et al., "Artificial Intelligence With Multi-Functional Machine Learning Platform Development for Better Healthcare and Precision Medicine," Database (Oxford), 2020, pp. 1-35, vol. 2020.
Davenport et al., "The Potential for Artificial Intelligence in Healthcare," Future Healthcare Journal, 2019, pp. 94-98, vol. 6, No. 2.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities For Artificial Intelligence to Transform How Care Is Delivered," Nov. 2019, American Hospital Association, pp. 1-12.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
"Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec 2017) (Year: 2017)".

(56) References Cited

OTHER PUBLICATIONS

Fuller, Carole G.; Diagnosis and treatment considerations with comorbid developmentally disabled populations; Journal of Clinical Psychology 54.1: 1-10. John Wiley and Sons Inc. (Jan. 1998) (Year: 1998).
He, Jianxing et al. The practical implementation of artificial intelligence technologies in medicine. Nature Medicine; New York vol. 25, Iss. 1. Jan 2019. (Year: 2019).
CG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC.2013.2262913. (Year: 2013).
H. Demirkan, "A Smart Healthcare Systems Framework," in IT Professional, vol. 15, No. 5, pp. 38-45, Sep.-Oct. 2013, doi: 10.1109/MITP.2013.35. (Year: 2013)
W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).
Amiya et al., "Is Exercise Training Appropriate for Patients With Advanced Heart Failure Receiving Continuous Inotropic Infusion? A Review," 2018, pp. 1-9, vol. 12, Japan.
Chu Hin Yee, "Physical Activity, Sedentary Behaviour and Health: From Measurements to Recommendations," 2018, 255 pages.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Chrif et al., "Control design for a lower-limb paediatric therapy device using linear motor technology," Article, 2017, pp. 119-127, Science Direct, Switzerland.
Robben et al., "Delta Features From Ambient Sensor Data are Good Predictors of Change in Functional Health," Article, 2016, pp. 2168-2194, vol. 21, No. 4, IEEE Journal of Biomedical and Health Informatics.
Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.
Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.
HCL Fitness, HCl Fitness PhysioTrainer Pro, 2017, retrieved on Aug. 19, 2021, 7 pages, https://www.amazon.com/HCl-Fitness-Physio Trainer-Electronically-Controlled/dp/B0759YMW78/.
International Preliminary Report on Patentability of International Application No. PCT/US2017/50895, Date of Mailing Dec. 11, 2018, 52 pages.
International Searching Authority, Search Report and Written Opinion for International Application No. PCT/US2017/50895, Date of Mailing Jan. 12, 2018, 6 pages.
International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
International Searching Authority, Search Report and Written Opinion for International Application No. PCT/US2021/032807, Date of Mailing Sep. 6, 2021, 11 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.
Marios et al., "The effect of tele-monitoring on exercise training adherence, functional capacity, quality of life and glycemic control in patients with type II diabetes," Journal of Sports Science and Medicine, Mar. 2012, vol. 11, 6 pages.
Joudaki et al., "Using Data Mining to Detect Health Care Fraud and Abuse: A Review of Literature", Global Journal of Health Science, vol. 7, No. 1, 2015 (Year: 2015).
Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.
Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.
Marchal-Crespo et al., "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.
Karboub et al., "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.
Chrif et al., "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.
International Preliminary Report on Patentability of International Application No. PCT/2024/022550, Date of Mailing Sep. 6, 20, 2025, 7 pages.

* cited by examiner

SYSTEM AND METHOD FOR USING AN ARTIFICIAL INTELLIGENCE ENGINE TO ANONYMIZE COMPETITIVE PERFORMANCE RANKINGS IN A REHABILITATION SETTING

CROSS-REFERENCES TO RELATED APPLICATIONS

This application is a continuation-in-part of U.S. patent application Ser. No. 17/739,906 filed May 9, 2022, titled "Systems and Methods for Using Machine Learning to Control an Electromechanical Device Used for Prehabilitation, Rehabilitation, and/or Exercise", which is a continuation of U.S. patent application Ser. No. 17/150,938, filed Jan. 15, 2021, titled "Systems and Methods for Using Machine Learning to Control an Electromechanical Device Used for Prehabilitation, Rehabilitation, and/or Exercise", which is a continuation-in-part of U.S. patent application Ser. No. 17/021,895, filed Sep. 15, 2020, titled "Telemedicine for Orthopedic Treatment", which claims priority to and the benefit of U.S. Provisional Patent Application Ser. No. 62/910,232, filed Oct. 3, 2019, titled "Telemedicine for Orthopedic Treatment", the entire disclosures of which are hereby incorporated by reference for all purposes.

This application also claims priority to and the benefit of U.S. Provisional Patent Application Ser. No. 63/217,052, filed Jun. 30, 2021, titled "System and Method for Using an Artificial Intelligence Engine to Anonymize competitive Performance Rankings in a Rehabilitation Setting", the entire disclosure of which is hereby incorporated by reference for all purposes.

BACKGROUND

Remote medical assistance, or telemedicine, may aid a patient in performing various aspects of a rehabilitation regimen for a body part. The patient may use a patient interface in communication with an assistant interface for receiving the remote medical assistance via audio, visual, and/or audiovisual communications.

SUMMARY

This disclosure relates generally to the fields of remote medical assistance and machine learning. Machine learning is generally defined as a field of computer science for discovering methodologies, algorithms, heuristics, and the like, whether in hardware, software or both, for the purpose of enabling computers or applications running on computers to learn without being explicitly programmed. Remote medical assistance, also referred to as, inter alia, remote medicine, telemedicine, telemed, telmed, tel-med, or telehealth, is generally defined as an at least two-way communication between a healthcare professional, provider or providers, such as a physician, physical therapist, a nurse, a chiropractor, etc., and a patient, wherein the two-way communication uses audio and/or audiovisual and/or other sensorial or perceptive (e.g., tactile, gustatory, haptic, pressure-sensing-based or electromagnetic (e.g., neurostimulatory) communications (e.g., via a computer, a smartphone, or a tablet).

Machine learning works through a variety of mechanisms, including iteration, optimization, pruning, testing, and the like. For example, a machine learning model may be trained on a set of training data, such that the model may be used to process newly or additionally received data to generate sets of predictions and/or classifications for various uses related to the discovery, investigation and generation of heuristic methods for the purpose of optimizing or improving a goal or outcome. Further, machine learning may preferably be continual or even continuous: The model developed for machine learning can always be further improved in light of the goals the model is trained to achieve. While machine learning could, in principle, be terminated at some point, then, in that case, the learning aspect would cease.

An aspect of the disclosed embodiments comprises a method for performing an exercise with an exercise apparatus. The method may comprise the steps of: receiving first patient data, wherein the first patient data includes at least a first patient identifier associated with the first patient and a first treatment plan including an exercise; receiving first measurement data, where the first measurement data is associated with a first performance data; receiving second measurement data, where the second measurement data is associated with at least one of a second performance data and a second patient identifier; one of anonymiztion of and pseudonymization of the second patient identifier; determining, via an artificial intelligence engine and based on one or more differences between the first and the second measurement data, differential data; and presenting, with a patient interface, at least one of the differential data, first measurement data, second measurement data, and the first patient data.

Another aspect of the present disclosure provides a system for performing an exercise with an exercise apparatus. The system may comprise a processing device and an artificial intelligence engine communicatively coupled to the processing device. The system may also include a memory including instruction that, when executed by the processing device, cause the processing device to: receive first patient data, wherein the first patient data includes at least a first patient identifier associated with the first patient and a first treatment plan including an exercise; receive first measurement data, where the first measurement data is associated with a first performance data; receive second measurement data, where the second measurement data is associated with at least one of a second performance data and a second patient identifier; anonymize the second patient identifier; and determine, via an artificial intelligence engine and based on one or more differences between the first and the second measurement data, differential data; and present, with a patient interface, a least one of the differential data, first measurement data, second measurement data, and the first patient data.

Another aspect of the disclosed embodiments comprises a tangible, non-transitory machine-readable medium storing instructions that, when executed, cause a processing device to perform any of the operations, steps, functions, and/or methods disclosed herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
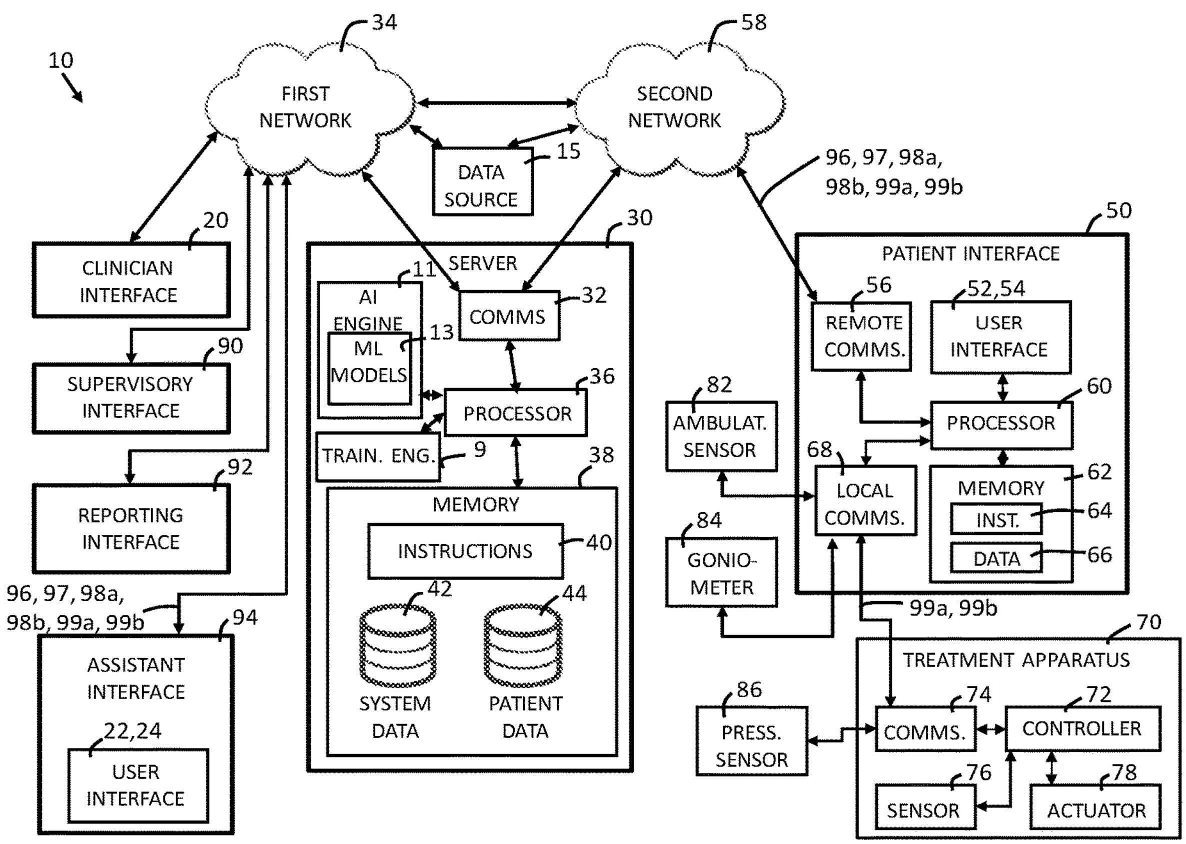
FIG. 1 generally illustrates a block diagram of an embodiment of a computer-implemented system for managing a treatment plan according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

The term "patient" may refer, without limitation, to an individual, a user, a student, a class participant, a human, a being, a living entity, etc. Both human and veterinary uses are included within the scope of this definition.

The term "treatment" may refer, without limitation, to a medical treatment, medical consultation for one or more conditions, training program, treatment for general health, non-medical treatments (e.g., treatments not necessarily indicated or prescribed by a healthcare provider, wherein such treatments are for the purpose of at least becoming more toned or muscular in appearance, to increase endurance, pliability, and the like), etc.

The term "healthcare service" may refer, without limitation, to healthcare services associated with one or more conditions for which the patient desires to maintain privacy, such as, e.g., services associated with conditions for which patients may prefer privacy (over conditions such as having a broken finger, or having the flu, etc., where privacy is often less important) like erectile dysfunction, sexually transmitted disease test results or diagnoses, hemorrhoids, ulcerative colitis, irritable bowel syndrome or disorder, Crohn's disease, diseases or conditions related to the genitourinary systems of males, female or other genders, gender reassignment surgery or medications and hormones prescribed and associated therewith; and/or, neurodegenerative diseases, orthopedic conditions and cancer diagnoses, treatments or conditions, mental health conditions, such as post-traumatic stress disorder, generalized anxiety, depression, bipolar disorder, schizophreniform disorders, eating disorders, disorders related to paraphilias, borderline personality disorder; and/or, cardiovascular conditioning, physical conditioning, weight lifting, or any other non-necessary medical treatment; and/or any other suitable mental health condition and any other service where privacy is mandated by law or requested by the patient.

A "treatment plan" may refer, without limitation, to one or more treatment protocols, and each treatment protocol may include one or more treatment sessions. Each treatment session may comprise several session periods, with each session period including a particular exercise for treating the body part of the patient. For example, a treatment plan for post-operative rehabilitation after a knee surgery may include an initial treatment protocol with twice daily stretching sessions for the first three (3) days after surgery and a more intensive treatment protocol with active exercise sessions performed four (4) times per day starting two (2) days after surgery. A treatment plan may also include information pertaining to a medical procedure to perform on the patient, a treatment protocol for the patient using an exercise apparatus, a diet regimen for the patient, a medication regimen for the patient, a sleep regimen for the patient, additional regimens, or some combination thereof.

The terms telemedicine, telehealth, telemed, teletherapeutic, remote medicine, etc. may be used interchangeably herein.

The term "condition" may be used to refer to a disease, a state or any other attribute of the user.

The term "remote medical assistance" may refer, without limitation, to remote medicine, telemedicine, telemed, telmed, tel-med, or telehealth, is an at least two-way communication between a healthcare provider or providers, such as a physician or a physical therapist, and a patient using audio and/or audiovisual and/or other sensorial or perceptive (e.g., tactile, gustatory, haptic, pressure-sensing-based or electromagnetic (e.g., neurostimulation) communications (e.g., via a computer, a smartphone, or a tablet).

The term "healthcare professional" or "healthcare provider" may refer, without limitation, to a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare professional" may be a human being, a robot, a virtual assistant, a virtual assistant in virtual and/or augmented reality, or an artificially intelligent entity, such entity including a software program, integrated software and hardware, or hardware alone; a doctor, physician assistant, nurse, chiropractor, dentist, physical therapist, acupuncturist, physical trainer, coach, personal trainer, neurologist, cardiologist, or the like (the "Fields of Practice"), and, without limitation, the "healthcare provider" may further refer to any person with a credential, license, degree, or the like in the field of medicine, physical therapy, rehabilitation, fitness, sports training, any other field relating to or associated with the Fields of Practice, or the like The term "anonymization" may refer, without limitation, to the meaning of the term "anonymization" and/or the meaning of the term "anonymisation," as these may otherwise have different meanings in, e.g., the United States vs. Europe.

The term "anonymous" may refer, without limitation, to an inability to trace or re-identify the patient's identity.

The term "pseudonymization" may refer, without limitation, to the meaning of the term "pseudonymization" and/or the meaning of the term "pseudonymisation," as these may otherwise have different meanings in, e.g., the United States vs. Europe.

The term "pseudonymous" may refer to an ability to trace or re-identify the patent identity though a controlled means (e.g., such as via access by controlling entities to a controlled database), wherein the pseudomyization may have been effected by the use of one or more Privacy Enhancing Technologies (PETs)).

The term "enhanced reality" may refer, without limitation, to a user experience comprising one or more of augmented reality, virtual reality, mixed reality, immersive reality, or a combination of the foregoing (e.g., immersive augmented reality, mixed augmented reality, virtual and augmented immersive reality, and the like).

The term "augmented reality" may refer, without limitation, to an interactive user experience that provides an enhanced environment that combines elements of a real-world environment with computer-generated components perceivable by the user.

The term "virtual reality" may refer, without limitation, to a simulated interactive user experience that provides an enhanced environment perceivable by the user and wherein such enhanced environment may be similar to or different from a real-world environment.

The term "mixed reality" may refer, without limitation, to an interactive user experience that combines aspects of augmented reality with aspects of virtual reality to provide a mixed reality environment perceivable by the user.

The term "immersive reality" may refer, without limitation, to a simulated interactive user experienced using virtual and/or augmented reality images, sounds, and other stimuli to immerse the user, to a specific extent possible (e.g., partial immersion or total immersion), in the simulated interactive experience. For example, in some embodiments, to the specific extent possible, the user experiences one or more aspects of the immersive reality as naturally as the user typically experiences corresponding aspects of the real-world. Additionally, or alternatively, an immersive reality experience may include actors, a narrative component, a theme (e.g., an entertainment theme or other suitable theme), and/or other suitable features of components.

The term "body halo" may refer, without limitation, to a hardware component or components, wherein such component or components may include one or more platforms, one or more body supports or cages, one or more chairs or seats, one or more back supports, one or more leg or foot engaging mechanisms, one or more arm or hand engaging mechanisms, one or more neck or head engaging mechanisms, other suitable hardware components, or a combination thereof.

The term "enhanced environment" may refer, without limitation, to an enhanced environment in its entirety, at least one aspect of the enhanced environment, more than one aspect of the enhanced environment, or any suitable number of aspects of the enhanced environment.

The term "medical action(s)" may refer, without limitation, to any suitable action performed by the medical professional (e.g., or the healthcare professional), and such action or actions may include diagnoses, prescription of treatment plans, prescription of treatment devices, and the making, composing and/or executing of appointments, telemedicine sessions, prescriptions or medicines, telephone calls, emails, text messages, and the like.

The terms "correlate," "correlation," and the like may refer to any suitable correlation or correlative relationship, including a correlation coefficient (e.g., a statistical value indicating an amount of correlation) not equal to zero (i.e., where zero exactly means there is no statistical correlation whatsoever), or any suitably defined correlation coefficient.

As used herein, the term "electronic medical record, "EMR," "electronic health record," and/or "EHR" may refer, without limitation, to a record (e.g., one or more documents, one or more database entries, and like) that includes information about a health history of a patient, individual, user, and the like. For example, the EMR may include information associated with one or more of diagnoses, medicines, tests, allergies, immunizations, treatment plans, any suitable characteristics associated with the patient (e.g., patient, individual, user, and the like), any suitable conditions associated with the patient (e.g., patient, individual, user, and the like), and the like.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures, including medical diagnostic procedures, non-diagnostic medical procedures, and non-medical-related interventions, to create an optimal treatment plan for a patient having certain characteristics (e.g., vital-sign or other measurements; performance; demographic; psychographic; geographic; diagnostic; measurement- or test-based; medically historic; etiologic; cohort-associative; differentially diagnostic; surgical, physically therapeutic, behavioral, pharmacologic and other treatment(s) recommended; etc.) may be a technically challenging problem. For example, a multitude of information or data may be considered when determining a treatment plan, which may result in inefficiencies and inaccuracies in the treatment plan selection process. In rehabilitative and non-rehabilitative (e.g., exercise or fitness) setting, some of the multitude of information considered may include characteristics of the patient such as personal information, performance information, and measurement information associated. The personal information or personal data may be associated with and/or include, e.g., demographic, psychographic or other information, such as an age, a weight, a gender, a height, a body mass index, a medical condition, a familial medication history, an injury, a medical procedure, a medication prescribed, or some combination thereof. The performance information or performance data may be associated with and/or include, e.g., an elapsed time of using a treatment device or exercise apparatus, an amount of force exerted on a portion of the treatment device, a range of motion achieved on the treatment device or exercise apparatus, a movement speed of a portion of the treatment device, a duration of use of the treatment device, an indication of a plurality of pain levels using the treatment device, or some combination thereof. The measurement information or measurement data may be associated with or include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, training, or communicating with, via a computing device during a telemedicine, telehealth session or exercise related tele-class (e.g., remote weight lifting or cycling classes), a patient from a location different than a location at which the patient is located. An additional technical problem is controlling or enabling the control of, from the different location, a treatment device used by the patient at the location at which the patient is located. In one example, often after a patient undergoes rehabilitative surgery (e.g., knee surgery), a healthcare provider may prescribe a treatment device to the patient to use to perform a treatment protocol at their residence or any mobile location or temporary domicile. In one example, A trainer, such as a coach, may outline a treatment plan for a training regimen, for competitive or non-competitive purposes, where a patient may use a treatment device to perform the treatment protocol in a remote or mobile location, such as a patient's residence or training facility.

Additionally, or alternatively, the two or more healthcare professionals may treat the patient (e.g., for the same condition, different conditions, related conditions, and the like). For example, an orthopedic surgeon, a physical therapist, trainer, coach and/or one or more other healthcare professionals may cooperatively or independent treat or be responsible for treatment of the patient for the same condition or a related condition. Such healthcare professionals may be located remotely from the patient and/or one another.

When the healthcare provider is located in a different location from the patient and the treatment device, it may be technically challenging for the healthcare provider to monitor the patient's actual progress (as opposed to relying on the patient's word about their progress) using the treatment device, modify the treatment plan according to the patient's progress, adapt the treatment device to the personal characteristics of the patient as the patient performs the treatment plan, and the like. For example, when a trainer is located in a different location from a patient using a treatment device, it may be technically challenging for the trainer to monitor the patient's actual progress (as opposed to relying on the patient's word about their progress) while using the treatment device, modify the treatment plan according to the patient's progress, adapt the treatment device to the personal characteristics of the patient as the patient performs the treatment plan, and the like.

Yet another technical problem may include protecting personal healthcare information (PHI) associated with the patient. PHI is a type of Personal Identifying Information or PII. The PHI or PII may be associated with, for example, a patient using the treatment device to perform various exercises and/or a patient receiving at least one service associated with a treatment. The law or the patient may demand that the patient's PHI or PII be maintained as anonymous, or otherwise pseudonymous. Accordingly, the systems and methods described herein may be configured such that a patient may seek at least one healthcare service associated with a treatment for one or more conditions, while remaining anonymous or pseudonymous.

In some embodiments, the systems and methods described herein may be configured to generate and/or receive a patient identifier associated with the patient. The patient identifier may include alphanumeric and/or special character information (e.g., such as a unique character string comprising one or more alphanumeric characters and/or one or more special characters), and/or other suitable identifier or identifying information. Additionally, or alternatively, the patient identifier may be associated with one or more characteristics associated with the patient. The patient identifier may be associated with physiological information about the patient, medications currently being taken by the patient, and the like. The patient identifier may be associated with one or more of a past, a current and/or an expected performance level of one or more treatment plans that are associated with a patient. The systems and methods described herein may be configured to store, in a centralized database or other suitable location, the patient identifier. The systems and methods described herein may be configured to correlate the patient identifier with the patient.

For example, the systems and methods described herein may be configured to execute and be controlled by a PET engine that uses one or more PETs that control access to personally identifiable information (PII) associated with the patient identifier. Controlling access may refer to defining access, enabling access, disabling access, etc. "Access," as used in the foregoing, and as further explicated below, may further comprise means of de-identification or re-identification. In some embodiments, the PET engine may be configured to pseudonymize or anonymize the PII associated with the patient. In some embodiments, the PET engine may enable de-identification and/or re-identification of the PII associated with the patient. PETs, as used by the PET engine herein, may include, without limitation, differential privacy, homomorphic encryption, public key encryption, digital notarization, pseudonymization, pseudonymisation, anonymization, anonymisation, digital rights management, k-anonymity, I-diversity, synthetic data generation, suppression, generalization, identity management, and the introduction of noise into existing data or systems. Further, the foregoing may apply in either or both of classical and quantum computing environments, or in any mix thereof. In some embodiments, the one or more PETs may be configured to support aspects of at least one of the Health Insurance Portability and Accountability Act (HIPAA) requirements, Gramm-Leach-Bliley Act (GLBA) requirements, European General Data Protection Regulation (GDPR) requirements, other suitable requirements, or a combination thereof.

In some embodiments, the systems and methods described herein may be configured to identify, based on at least one healthcare service indicated by the patient, a healthcare provider associated with providing the at least one healthcare service. The at least one healthcare service may be included in the patient identifier, indicated by the patient using a user interface, or otherwise indicated by the patient.

In some embodiments, the at least one healthcare service may include any of the healthcare services described herein, any other suitable healthcare services, or a combination thereof. In some embodiments, the systems and methods described herein may be configured to identify, based on at least one of the at least one healthcare service and the identified healthcare provider, relevant information associated with the patient identifier. The relevant information may correspond to a healthcare service of cardiovascular-condition-improving cycling for training or rehabilitation.

In some embodiments, the systems and methods described herein may be configured to receive input from the patient, wherein the input indicates a selection of an option. For example, the patient may desire to provide further information related to the first electronic medical record to the healthcare provider. The input may be an indication to provide further information, or to make a selection.

In some embodiments, the healthcare provider may generate, for the patient, a treatment plan corresponding to one or more conditions of the patient. Typically, the patient may perform, using the treatment device, various aspects of the treatment plan, such as an exercise, to treat one or more conditions of the patient. For example, the patient may be recovering from an orthopedic surgery, a cardiac surgery, a neurological surgery, a gastrointestinal surgery, a genitourological surgery, a gynecological surgery, or other surgery and may use the treatment device to rehabilitate one or more affected portions of the patient's body. Alternatively, the patient may be recovering from a neurological surgery or a program to treat mental unwellness and may use the treatment device to rehabilitate neurological or other mental responses or brain functions which have a physical manifestation with regard to one or more directly or indirectly affected portions of the patient's body. Alternatively, the patient may be being treated for physical and/or mental conditions associated with post-traumatic stress disorder (PTSD) and may use the treatment device to rehabilitate neurological or other mental responses or brain functions, which have a physical manifestation. Further, the patient, while recovering from post-traumatic stress disorder, may use the treatment device to improve general mental health (e.g., through exercise, goal-oriented activity and achievement, and the like). Alternatively, the patient may be being treated for a somatoform disorder associated with PTSD or other trauma, injury, and the like. The patient may use the treatment device to rehabilitate neurological or other mental responses or brain functions, which have a physical manifestation and/or other mental manifestation. Such conditions may be referred to as primary conditions (e.g., conditions for which the patient uses the treatment device to perform the treatment plan). Similarly, the patient may use the treatment device to strength training aspects of the treatment plan or of any other strength training plan.

In some embodiments, during an adaptive telemedicine session, the systems and methods described herein may be configured to use artificial intelligence and/or machine learning to assign patients to cohorts and to dynamically control one or more treatment devices based on the assignment. The term "adaptive telemedicine" may refer to a telemedicine session that is dynamically adapted based on one or more factors, criteria, parameters, characteristics, or the like. The one or more factors, criteria, parameters, characteristics, or the like may pertain to the user (e.g., heartrate, blood pressure, perspiration rate, pain level, or the like), the treatment device (e.g., pressure, range of motion, speed of motor, etc.), details of the treatment plan, and so forth.

In some embodiments, numerous patients may be prescribed numerous treatment devices because the numerous patients are recovering from the same medical procedure, suffering from the same injury, and/or performing the same exercise. The numerous treatment devices may be provided to the numerous patients. The treatment devices may be used by the patients to perform treatment plans in their residences, at gyms, at rehabilitative centers, at hospitals, or at any suitable locations, including permanent or temporary domiciles.

In some embodiments, the treatment devices may be communicatively coupled to a server. Characteristics of the patients, including the treatment data, may be collected before, during, and/or after the patients perform the treatment plans. For example, any or each of the personal information, the performance information, and the measurement information may be collected before, during, and/or after a patient performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step or set of steps in the treatment plan. Such a technique may enable the determination of which steps in the treatment plan lead to desired results (e.g., improved muscle strength, range of motion, etc.) and which steps lead to diminishing returns (e.g., continuing to exercise after 3 minutes actually delays or harms recovery).

Performance data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The performance data that may be collected may include the characteristics of the patients, the treatment plans performed by the patients, the results of the treatment plans, any of the data described herein, any other suitable data, or a combination thereof.

In some embodiments, the performance data may be processed to group certain people into cohorts. The people may be grouped by people having certain or selected similar characteristics, treatment plans, and results of performing the treatment plans. For example, athletic people having no medical conditions who perform a treatment plan (e.g., use the treatment device for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. In some embodiments, the artificial intelligence engine may be used to identify trends and/or patterns and to define new cohorts based on achieving desired results from the treatment plans and machine learning models associated therewith may be trained to identify such trends and/or patterns and to recommend and rank the desirability of the new cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for one or more patients. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient. In some embodiments, the artificial intelligence engine may modify the treatment plan if the monitored data shows the plan to be inappropriate or counterproductive for the user.

In some embodiments, the treatment plans and/or excluded treatment plans may be presented to one or more patients, during a group telemedicine or group telehealth session, to a healthcare provider. The healthcare provider may select a particular treatment plan for one or more of the patients to cause that treatment plan to be transmitted to the collective patients or an individual patient and/or to control, based on the treatment plans, one or more treatment devices. In some embodiments, to facilitate telehealth or telemedicine applications, including remote diagnoses, determination of treatment plans and rehabilitative and/or pharmacologic prescriptions, the artificial intelligence engine may receive and/or operate distally from the patients and the treatment devices.

In such cases, the recommended treatment plans and/or excluded treatment plans may be presented simultaneously with a video of the patient in real-time or near real-time during a telemedicine or telehealth session on a user interface of a computing device of a healthcare provider. The video may also be accompanied by audio, text and other multimedia information. Real-time may refer to less than or equal to 2 seconds. Real-time may also refer to near real-time, which may be less than 10 seconds or any reasonably proximate difference between two different times. Additionally, or alternatively, near real-time may refer to any interaction of a sufficiently short time to enable two individuals to engage in a dialogue via such user interface and will generally be less than 10 seconds but greater than 2 seconds.

Presenting the treatment plans generated by the artificial intelligence engine concurrently with a presentation of the patient video may provide an enhanced user interface because the healthcare provider may continue to visually and/or otherwise communicate with the patient while also reviewing the treatment plans on the same user interface. The enhanced user interface may improve the healthcare provider's experience using the computing device and may encourage the healthcare provider to reuse the user interface. Such a technique may also reduce computing resources (e.g., processing, memory, network) because the healthcare provider does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare provider may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

A technical problem may occur which relates to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various healthcare providers may be installed on their local computing devices and may use proprietary formats. Accordingly, some embodiments of the present disclosure may use an API to obtain, via interfaces exposed by APIs used by the sources, the formats used by the sources. In some embodiments, when information is received from the sources, the API may map, translate and/or convert the format used by the sources to a standardized format used by the artificial intelligence engine. Further, the information mapped, translated and/or converted to the standardized format used by the artificial intelligence engine may be stored in a database accessed by the artificial intelligence engine when performing any of the techniques disclosed herein. Using the information mapped, translated and/or converted to a standardized format may enable the more accurate determination of the procedures to perform for the patient and/or a billing sequence.

To that end, the standardized information may enable the generation of treatment plans and/or billing sequences having a particular format configured to be processed by various applications (e.g., telehealth). For example, applications, such as telehealth applications, may be executing on various computing devices of medical professionals and/or patients. The applications (e.g., standalone or web-based) may be provided by a server and may be configured to process data according to a format in which the treatment plans are implemented. Accordingly, the disclosed embodiments may provide a technical solution by (i) receiving, from various sources (e.g., EMR systems), information in non-standardized and/or different formats; (ii) standardizing the information; and (iii) generating, based on the standardized information, treatment plans having standardized formats capable of being processed by applications (e.g., telehealth applications) executing on computing devices of medical professional and/or patients.

With reference to the FIGS., FIG. 1 generally illustrates a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store (e.g. write to an associated memory) and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store patient data, performance data, or like the like regarding a patient in following a treatment plan. For example, the memory 38 includes a patient data store 44 configured to hold patient data, such as data pertaining to the one or more patients, including data representing each patient's performance within the treatment plan.

Additionally or alternatively, the characteristics (e.g., personal, performance, measurement, etc.) of the people, the treatment plans followed by the patients, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices and/or digital storage media over time and stored in the data store 44. The characteristic data, treatment plan data, and results data may be correlated in the patient-cohort databases in the patient data store 44. The characteristics of the people may include PHI, PII, other personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control an exercise apparatus 70, among other things. The machine learning models 13 may be trained to generate, based on data associated with a diagnosis of users, initial treatment plans to be performed on the exercise apparatus 70 by the users. For example, the machine learning models 13 may be trained to provide a visual stimulus, audio stimulus, or haptic stimulus.

The machine learning models 13 may be trained to generate, based on data associated with a diagnosis of users, desired goal of the user(s), initial treatment plans to be performed on the exercise apparatus 70 by the users. For example, the machine learning models 13 may be trained to provide a visual stimulus, audio stimulus, or haptic stimulus.

The server (also refereed herein as a processing device) 30 may receive first patient data, where the first patient data includes at least a first patient identifier associated with the first patient and a first treatment plan. For example, for example the processing device may receive a first patient identifier that is associated with a resistance level of an exercise apparatus, where the resistance level is defined by a first treatment plan. The processing device 30 may also receive second patient data, wherein the second patient data includes a second patient identifier associated with the second patient and a second treatment plan. For example, the processing deice 30 may receive a second patient identifier that is associated with a resistance level of an exercise apparatus, where the resistance level is associated with a second treatment plan. The first and the second treatment plans may include characteristic that are identical to one another, or that differ.

The processing device 30 may also receive first and second measurement data associated with respective performance levels of the treatment plans by the respective patients. For example the processing device 30 may receive measurement data associated with a rate of rotation of the pedals for each patient. The measurement data may be from a current or past treatment plan. In some embodiments, the first and/or second patient identifier may be anonymized. The anonymized or pseudonymized may be completed by the server 30 and/or the AI engine 11, or by cooperation between the server 30 and the AI engine 11. The anonymized or pseudonymized may also occur to a single patient identifiers, when the patient identifier comprises more than one characteristic.

The AI engine 11, based on a variance of one or more of the first and the second measurement data and first and second patient data, may determine differential data. For example, the AI engine 11 may determine differential data associated with a difference between the rate of rotation of between the first and the second patients. In another example, the AI engine may determine differential data associated with a performance level of the first or the second patient that is outside a pre-determined threshold rate of rotation (e.g., the variance between the rotation rate should not be more than 10 rotations per minute). The differential data may also be based on a variance of measurement data associated with any number of current, past, and/or anticipated measurement data.

The AI engine 11 may generate, based on the differential data, an instruction to modify at least one of the first and the second exercises. For example, if the differential data identifies a rate of rotation that exceeds the pre-determined threshold rate of rotation, the AI engine 11 may generate instruction increase and/or decrease the resistance of the first or the second patient. In response, the AI engine 11, user, and/or server 30 may control, based on the differential data, at least one of the first and the second exercise apparatus. For example, the AI engine 11 may instruct the exercise apparatus 70 to increase or decrease a resistance. The controlling may comprise of a modification to any number of operating states of the exercise. For example, the positions of the exercise apparatus 70 may be adjusted (e.g., become closer or further from the patient), a resistance, weight, etc. may be modified.

The machine learning models 13 may also be configured, for example, to display on a user interface or otherwise inform the user of a goal for the day, where the goal is dependent upon the generated treatment plan. For example, the machine learning models may be configured to request a measurement of a vital sign of the user, a respiration rate of the user, a heartrate of the user, a heart rhythm of a user, an oxygen saturation of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the exercise apparatus 70, an amount of force exerted on a portion of the exercise apparatus 70, a range of motion achieved on the exercise apparatus 70, a movement speed of a portion of the exercise apparatus 70, a pressure exerted on a portion of the exercise apparatus 70, a movement acceleration of a portion of the exercise apparatus 70, a movement jerk of a portion of the exercise apparatus 70, a torque level of a portion of the exercise apparatus 70, and an indication of a plurality of pain levels experienced by the user when using the exercise apparatus 70. The requested metric may require an input of sensor data or, in some embodiment, may only require manual entry by the user. In some embodiments, the metrics that the machine learning models 13 are trained to monitor are related to the underlying condition or attribute of the user. In other embodiments, the metric that the machine learning models 13 are trained to monitor are related to an underlying condition of the user.

The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 9 may be cloud-based or a real-time software platform, and it may include privacy software or protocols, and/or security software or protocols.

To train the one or more machine learning models 13, the training engine 9 may use a training data set of a corpus of the characteristics (e.g., medical diagnoses, attributes, a measurement of a vital sign of the user, a respiration rate of the user, a heartrate of the user, a heart rhythm of a user, an oxygen saturation of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the exercise apparatus 70, an amount of force exerted on a portion of the exercise apparatus 70, a range of motion achieved on the exercise apparatus 70, a movement speed of a portion of the exercise apparatus 70, a pressure exerted on a portion of the exercise apparatus 70, a movement acceleration of a portion of the exercise apparatus 70, a movement jerk of a portion of the exercise apparatus 70, a torque level of a portion of the exercise apparatus 70, an indication of a plurality of pain levels experienced by the user when using the exercise apparatus 70, etc.) of the people that used the exercise apparatus 70 to perform treatment plans, the details (e.g., treatment protocol including exercises, amount of time to perform the exercises, how often to perform the exercises, a schedule of exercises, parameters/configurations/settings of the exercise apparatus 70 throughout each step of the treatment plan, etc.) of the treatment plans performed by the people using the exercise apparatus 70, and the results of the treatment plans performed by the people. The one or more machine learning models 13 may be trained to match patterns of characteristics of a patient with characteristics of other people in assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, treatment apparatus 70. The one or more machine learning models 13 may also be trained to provide one or more treatment plan options to a healthcare professional to select from and to control the exercise apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.). In some embodiments, the patient interface 50 may include functionality provided by or similar to existing voice-based assistants such as Siri by Apple, Alexa by Amazon, Google Assistant, or Bixby by Samsung.

As generally illustrated in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes an exercise apparatus 70 configured to be manipulated by the patient and/or to manipulate a body part of the patient for performing activities according to the treatment plan. In some embodiments, the exercise apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The exercise apparatus 70 may be any suitable medical, rehabilitative, therapeutic, etc. apparatus configured to be controlled distally via another computing device to treat a patient and/or exercise the patient. The exercise apparatus 70 may be an electromechanical machine including one or more weights, an electromechanical bicycle, an electromechanical spin-wheel, a smart-mirror, a treadmill, an interactive environment system or the like. The body part may include, for example, a spine, a hand, a foot, a knee, or a shoulder. The body part may include a part of a joint, a bone, or a muscle group, such as one or more vertebrae, a tendon, or a ligament. As generally illustrated in FIG. 1, the exercise apparatus 70 includes a controller 72, which may include one or more processors, computer memory, and/or other components. The exercise apparatus 70 also includes a fourth communication interface 74 configured to communicate with the patient interface 50 via the local communication interface 68. The exercise apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the exercise apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the exercise apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the exercise apparatus 70.

The system 10 generally illustrated in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 generally illustrated in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 generally illustrated in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 generally illustrated in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 generally illustrated in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 a healthcare professional, such as those described herein, to remotely communicate with the patient interface 50 and/or the exercise apparatus 70. Such remote communications may enable the assistant to provide assistance or guidance to a patient using the system 10. More specifically, the assistant interface 94 is configured to communicate a telemedicine signal 96, 97, 98*a*, 98*b*, 99*a*, 99*b* with the patient interface 50 via a network connection such as, for example, via the first network 34 and/or the second network 58. The telemedicine signal 96, 97, 98*a*, 98*b*, 99*a*, 99*b* comprises one of an audio signal 96, an audiovisual signal 97, an interface control signal 98*a* for controlling a function of the patient interface 50, an interface monitor signal 98*b* for monitoring a status of the patient interface 50, an apparatus control signal 99*a* for changing an operating parameter of the exercise apparatus 70, and/or an apparatus monitor signal 99*b* for monitoring a status of the exercise apparatus 70. In some embodiments, each of the control signals 98*a*, 99*a* may be unidirectional, conveying commands from the assistant interface 94 to the patient interface 50. In some embodiments, in response to successfully receiving a control signal 98*a*, 99*a* and/or to communicate successful and/or unsuccessful implementation of the requested control action, an acknowledgement message may be sent from the patient interface 50 to the assistant interface 94. In some embodiments, each of the monitor signals 98*b*, 99*b* may be unidirectional, status-information commands from the patient interface 50 to the assistant interface 94. In some embodiments, an acknowledgement message may be sent from the assistant interface 94 to the patient interface 50 in response to successfully receiving one of the monitor signals 98*b*, 99*b*.

In some embodiments, the patient interface 50 may be configured as a pass-through for the apparatus control signals 99*a* and the apparatus monitor signals 99*b* between the exercise apparatus 70 and one or more other devices, such as the assistant interface 94 and/or the server 30. For example, the patient interface 50 may be configured to transmit an apparatus control signal 99*a* in response to an apparatus control signal 99*a* within the telemedicine signal 96, 97, 98*a*, 98*b*, 99*a*, 99*b* from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98*a*, 98*b*, 99*a*, 99*b* may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the healthcare professional may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the healthcare professional to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the healthcare professional. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, in response to a verbal command by the patient (which may be given in any one of several different languages), the system 10 may automatically initiate a telemedicine In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the exercise apparatus 70 may each operate from a patient location geographically separate from a location of the assistant interface 94. For example, the patient interface 50 and the exercise apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an healthcare professional remotely from any conventional office infrastructure. Such remote work may be performed, for example, where the assistant interface 94 takes the form of a computer and/or telephone. This remote work functionality may allow for work-from-home arrangements that may include part time and/or flexible work hours for an healthcare professional.

Figure 2:
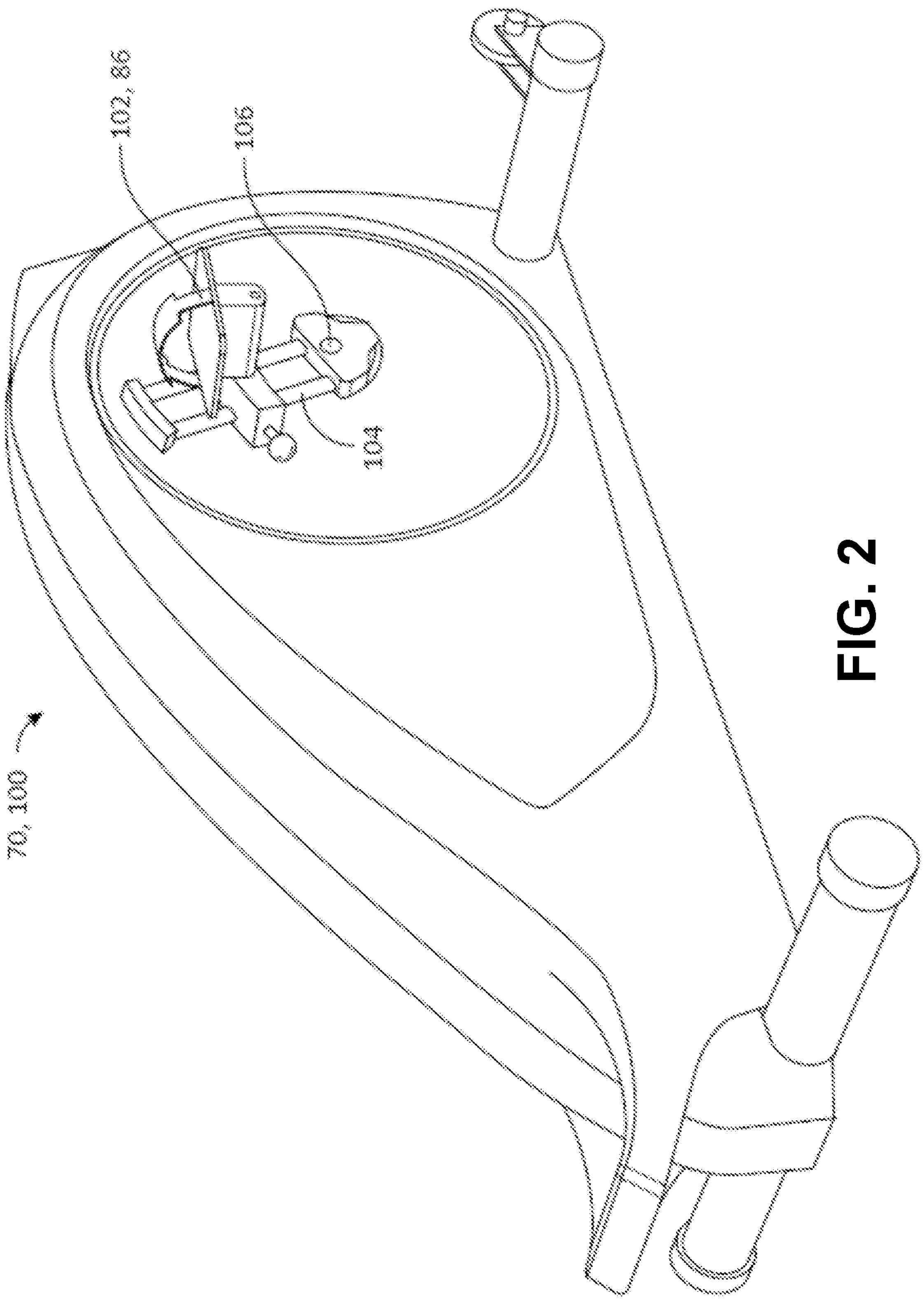
FIG. 2 generally illustrates a perspective view of an embodiment of an exercise apparatus according to the principles of the present disclosure.
Figure 3:
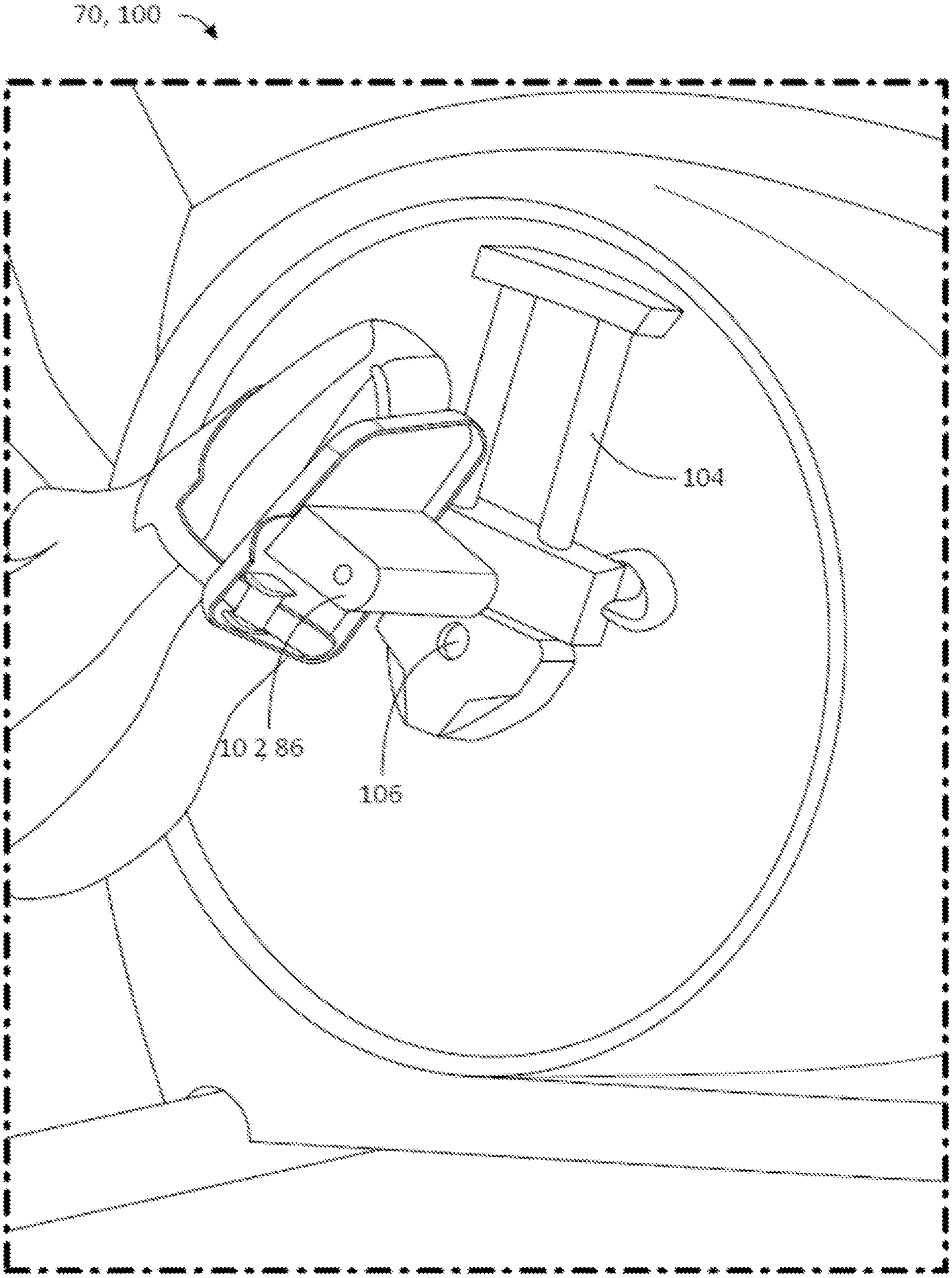
FIG. 3 generally illustrates a perspective view of a pedal of the exercise apparatus of FIG. 2 according to the principles of the present disclosure.

FIGS. 2-3 show an embodiment of an exercise apparatus 70. More specifically, FIG. 2 generally illustrates an exercise apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as generally illustrated in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. One or more pressure sensors 86 is attached to or embedded within one or both of the pedals 102 for measuring an amount of force applied by the patient on a pedal 102. The pressure sensor 86 may communicate wirelessly to the exercise apparatus 70 and/or to the patient interface 50.

Figure 4:
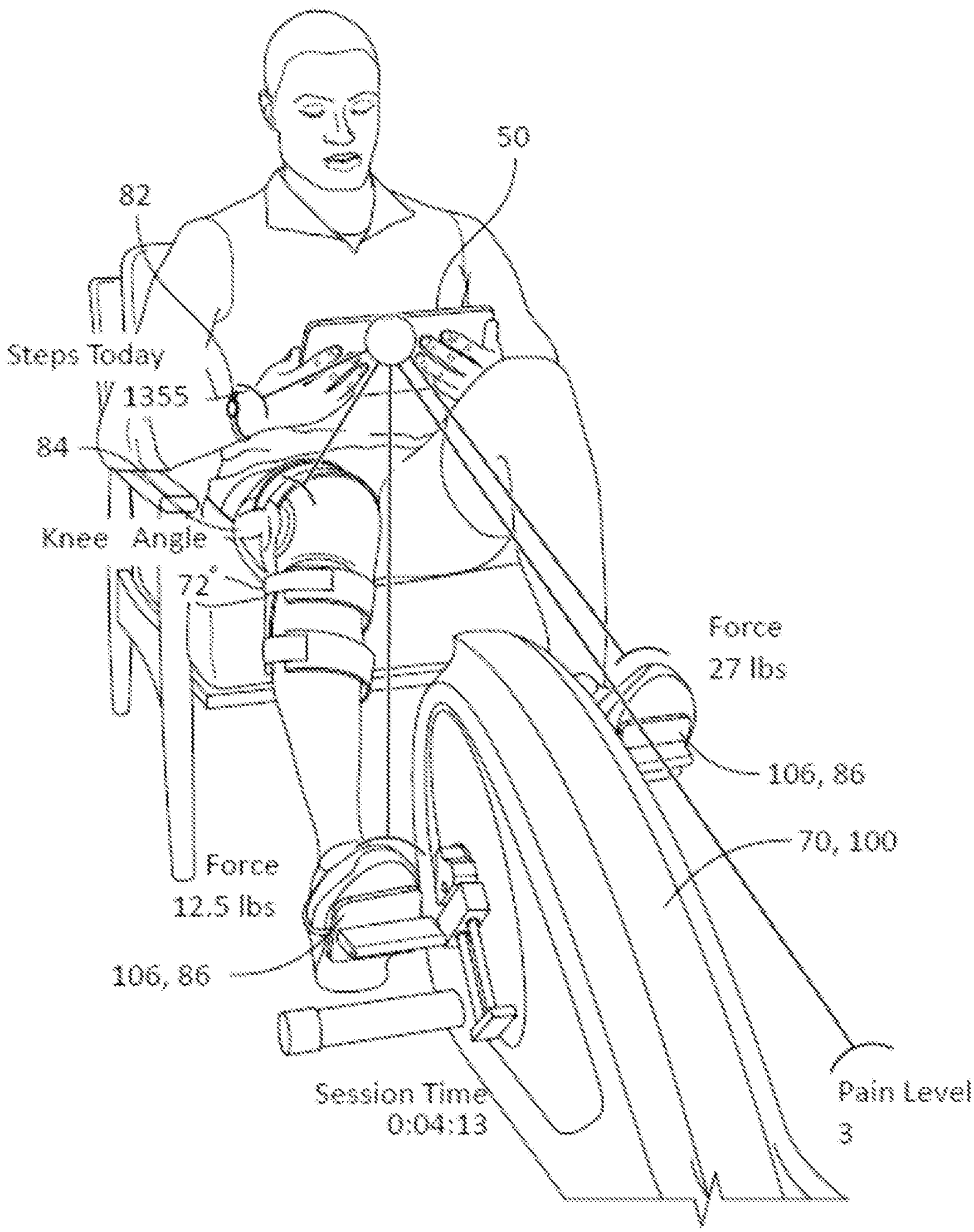
FIG. 4 generally illustrates a perspective view of a person using the exercise apparatus of FIG. 2 according to the principles of the present disclosure.

FIG. 4 generally illustrated a person (a patient) using the exercise apparatus 70 of FIG. 2, and generally illustrating sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the exercise apparatus 70. FIG. 4 generally illustrates the patient wearing the ambulation sensor 82 on his wrist, with a note showing "STEPS TODAY 1355", indicating that the ambulation sensor 82 has recorded and transmitted that step count to the patient interface 50. FIG. 4 also generally illustrates the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the exercise apparatus 70 for 4 minutes and 13 seconds. This session time may be determined by the patient interface 50 based on information received from the exercise apparatus 70. FIG. 4 also generally illustrates an indicator showing "PAIN LEVEL 3". Such a pain level may be obtained from the patent in response to a solicitation, such as a question, presented upon the patient interface 50.

Additionally or alternatively, one of more remote sensing devices 108 may be spaced from the user for remotely detecting vital signs of the user. The one or more remote sensing devices 108 may include any one of or a combination of the sensors shown in FIG. 4 attached to the user's body or the exercise apparatus 70, but configured to remotely monitor the desired feedback. For example, the remote sensing devices 108 may include a high-definition camera or an infrared camera connected to or integrated with analytical software, such as motion-capture software or facial-recognition software. The remote sensing devices 108 may also be configured to detect the location of at least one node, or marker, placed on the user or the exercise apparatus 70, to detect a speed or number of repetitions that have been completed by the user. By way of example, the remote sensing devices 108 may detect that the a node attached to the right knee of the user moves sporadically (e.g. deviates from an expected motion) while the user uses the exercise apparatus 70. Alternatively or additionally, the remote sensing devices 108 may be configured to detect the temperature or perspiration, of the user. In some embodiments, the remote sensing devices 108 and their associated software are configured to identify a level of strain the user undergoes while the user uses the treatment device. For example, the one or more remote sensing devices 108 may implement facial recognition to detect a change in the physical appearance of the user (e.g., wrinkling of the skin around the user's eyes, clenching of the user's jaw).

Figure 5:
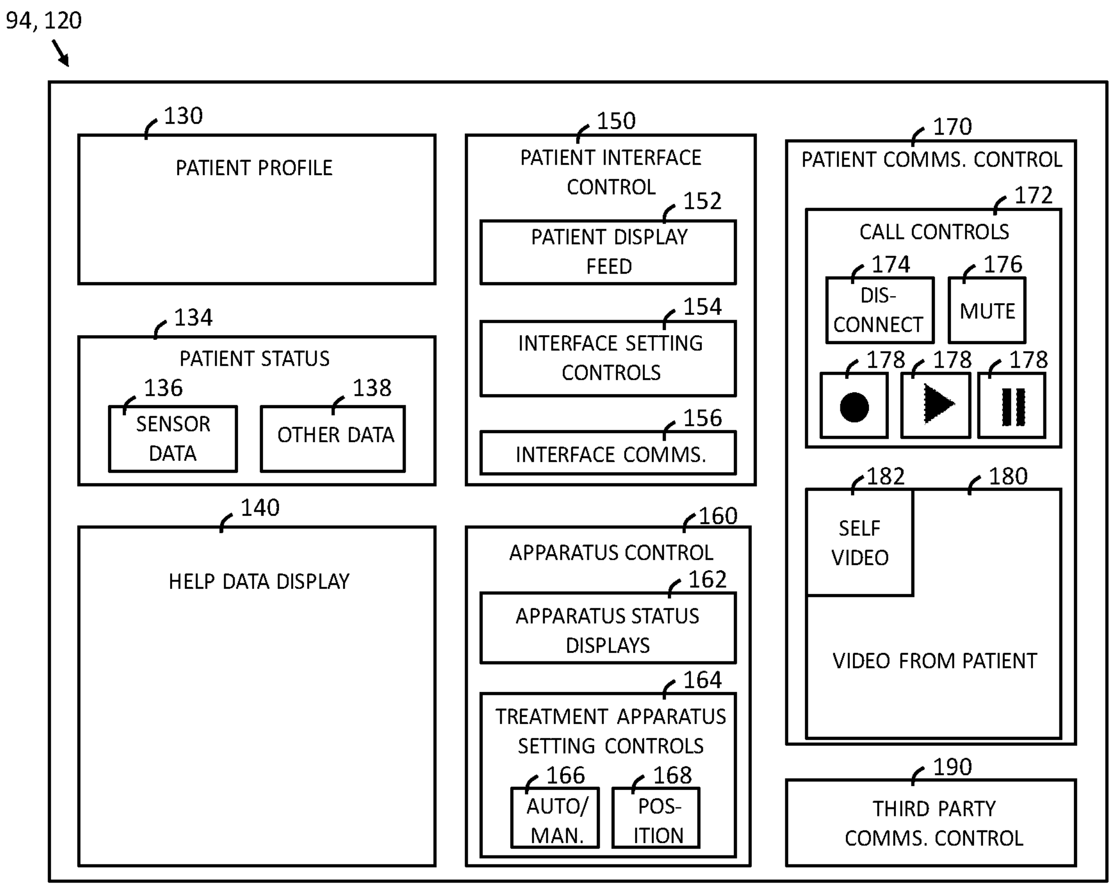
FIG. 5 generally illustrates an example embodiment of an overview display of an assistant interface according to the principles of the present disclosure.

FIG. 5 is an example embodiment of an overview display 120 of the assistant interface 94. Specifically, the overview display 120 presents several different controls and interfaces for the healthcare professional to remotely assist a patient with using the patient interface 50 and/or the exercise apparatus 70. This remote assistance functionality may also be called telemedicine or telehealth.

Specifically, the overview display 120 includes a patient profile display 130 presenting biographical information regarding a patient using the exercise apparatus 70. The patient profile display 130 may take the form of a portion or region of the overview display 120, as generally illustrated in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the healthcare professional's need for that information. For example, a healthcare professional that is assisting the patient with a medical issue may be provided with medical history information regarding the patient, whereas a technician troubleshooting an issue with the exercise apparatus 70 may be provided with a much more limited set of information regarding the patient. The technician, for example, may be given only the patient's name. The patient profile display 130 may include pseudonym zed data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the exercise apparatus 70. Such treatment plan information may be limited to a healthcare professional. For example, a healthcare professional assisting the patient with an issue regarding the treatment regimen may be provided with treatment plan information, whereas a technician troubleshooting an issue with the exercise apparatus 70 may not be provided with any information regarding the patient's treatment plan.

In some embodiments, one or more recommended treatment plans and/or excluded treatment plans may be presented in the patient profile display 130 to the healthcare professional. The one or more recommended treatment plans and/or excluded treatment plans may be generated by the artificial intelligence engine 11 of the server 30 and received from the server 30 in real-time during a telemedicine or telehealth session. An example of presenting the one or more recommended treatment plans and/or ruled-out treatment plans is described below with reference to FIG. 7.

The example overview display 120 generally illustrated in FIG. 5 also includes a patient status display 134 presenting status information regarding a patient using the exercise apparatus 70. The patient status display 134 may take the form of a portion or region of the overview display 120, as generally illustrated in FIG. 5, although the patient status display 134 may take other forms, such as a separate screen or a popup window. The patient status display 134 includes sensor data 136 from one or more of the external sensors 82, 84, 86, and/or from one or more internal sensors 76 of the exercise apparatus 70. In some embodiments, the patient status display 134 may include sensor data from one or more sensors of one or more wearable devices worn by the patient or spaced from the patient (i.e., the remote sensing devices 108) while using the exercise apparatus 70. The one or more wearable devices may include a watch, a bracelet, a necklace, a chest strap, and the like. The one or more wearable devices may be configured to monitor a heartrate, a temperature, a blood pressure, one or more vital signs, and the like of the patient while the patient is using the exercise apparatus 70. The one or more remote sensing devices 108 may be configured to interact with or communicate with the wearable devices in order to more particularly identify attributes of the user. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the healthcare professional/user's need for and/or qualifications to view that information.

The example overview display 120 generally illustrated in FIG. 5 also includes a help data display 140 presenting information for the healthcare professional to use in assisting the patient. The help data display 140 may take the form of a portion or region of the overview display 120, as generally illustrated in FIG. 5. The help data display 140 may take other forms, such as a separate screen or a popup window. The help data display 140 may include, for example, presenting answers to frequently asked questions regarding use of the patient interface 50 and/or the exercise apparatus 70. The help data display 140 may also include research data or best practices. In some embodiments, the help data display 140 may present scripts for answers or explanations in response to patient questions. In some embodiments, the help data display 140 may present flow charts or walk-throughs for the healthcare professional to use in determining a root cause and/or solution to a patient's problem. In some embodiments, the assistant interface 94 may present two or more help data displays 140, which may be the same or different, for simultaneous presentation of help data for use by the healthcare professional. for example, a first help data display may be used to present a troubleshooting flowchart to determine the source of a patient's problem, and a second help data display may present script information for the healthcare professional to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 generally illustrated in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As generally illustrated in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the healthcare professional to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the healthcare professional to remotely view and/or control the patient interface 50. For example, the patient interface setting control 154 may enable the healthcare professional to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the healthcare professional to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare professional to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare professional to change the font size setting of the patient interface 50.

The example overview display 120 generally illustrated in FIG. 5 also includes an interface communications display 156 showing the status of communications between the patient interface 50 and one or more other devices 70, 82, 84, such as the exercise apparatus 70, the ambulation sensor 82, and/or the goniometer 84. The interface communications display 156 may take the form of a portion or region of the overview display 120, as generally illustrated in FIG. 5. The interface communications display 156 may take other forms, such as a separate screen or a popup window. The interface communications display 156 may include controls for the healthcare professional to remotely modify communications with one or more of the other devices 70, 82, 84. For example, the healthcare professional may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 generally illustrated in FIG. 5 also includes an apparatus control 160 for the healthcare professional to view and/or to control information regarding the exercise apparatus 70. The apparatus control 160 may take the form of a portion or region of the overview display 120, as generally illustrated in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the exercise apparatus 70 is currently communicating with the patient interface 50. The apparatus status display 162 may present other current and/or historical information regarding the status of the exercise apparatus 70.

The apparatus control 160 may include an apparatus setting control 164 for the healthcare professional to adjust or control one or more aspects of the exercise apparatus 70. The apparatus setting control 164 may cause the assistant interface 94 to generate and/or to transmit an apparatus control signal 99 (e.g. which may be referred to as treatment plan input) for changing an operating parameter and/or one or more characteristics of the exercise apparatus 70, (e.g., a pedal radius setting, a resistance setting, a target RPM, other suitable characteristics of the treatment device 70, or a combination thereof). The apparatus setting control 164 may include a mode button 166 and a position control 168, which may be used in conjunction for the healthcare professional to place an actuator 78 of the exercise apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the healthcare professional may change an operating parameter of the exercise apparatus 70, such as a pedal radius setting, while the patient is actively using the exercise apparatus 70. Such "on the fly" adjustment may or may not be available to the patient using the patient interface 50. In some embodiments, the apparatus setting control 164 may allow the healthcare professional to change a setting that cannot be changed by the patient using the patient interface 50. For example, the patient interface 50 may be precluded from changing a preconfigured setting, such as a height or a tilt setting of the exercise apparatus 70, whereas the apparatus setting control 164 may provide for the healthcare professional to change the height or tilt setting of the exercise apparatus 70.

The example overview display 120 generally illustrated in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the healthcare professional while the healthcare professional uses the assistant interface 94. Alternatively or additionally, the audio and/or audiovisual communications may include communications with a third party. For example, the system 10 may enable the healthcare professional to initiate a 3-way conversation regarding use of a particular piece of hardware or software, with the patient and a subject matter expert, such as a medical professional or a specialist. The example patient communications control 170 generally illustrated in FIG. 5 includes call controls 172 for the healthcare professional to use in managing various aspects of the audio or audiovisual communications with the patient. The call controls 172 include a disconnect button 174 for the healthcare professional to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session (e.g., which may be referred to herein as the virtual conference room). The call controls 172 also include a video feed display 180 for presenting still and/or video images from the patient interface 94, and a self-video display 182 showing the current image of the healthcare professional using the assistant interface 94. The self-video display 182 may be presented as a picture-in-picture format, within a section of the video feed display 180, as generally illustrated in FIG. 5. Alternatively or additionally, the self-video display 182 may be presented separately and/or independently from the video feed display 180.

The example overview display 120 generally illustrated in FIG. 5 also includes a third party communications control 190 for use in conducting audio and/or audiovisual communications with a third party. The third party communications control 190 may take the form of a portion or region of the overview display 120, as generally illustrated in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include conference calling capability for the third party to simultaneously communicate with both the healthcare professional via the assistant interface 94, and with the patient via the patient interface 50. For example, the system 10 may provide for the healthcare professional to initiate a 3-way conversation with the patient and the third party.

Figure 6:
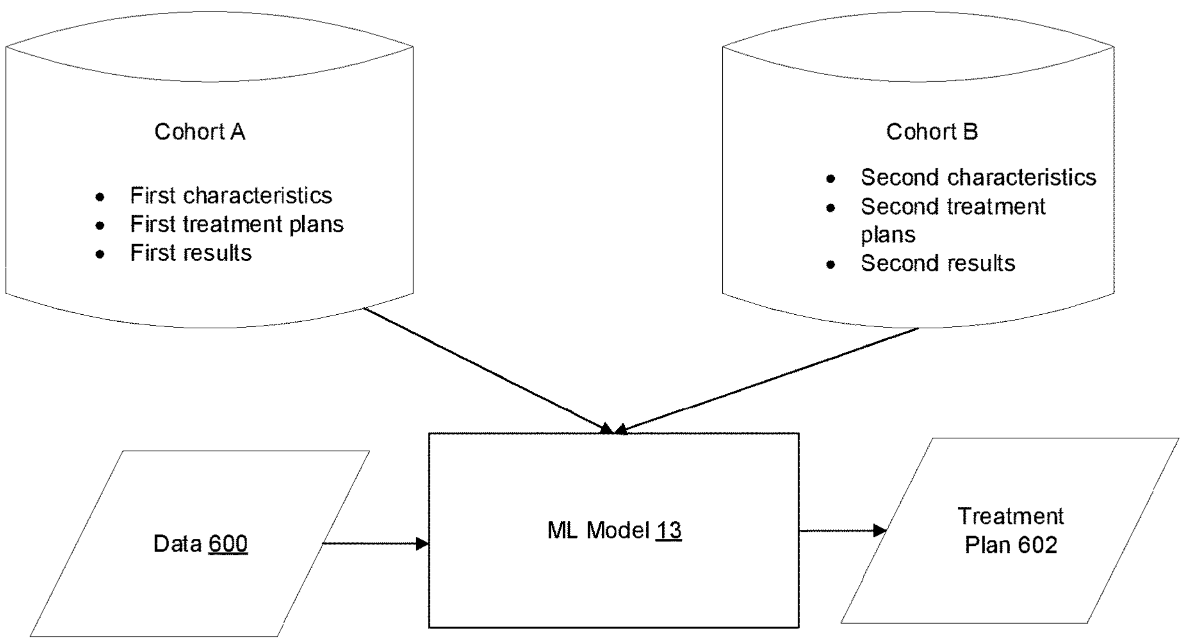
FIG. 6 generally illustrates an example block diagram of training a machine learning model to output, based on data pertaining to the patient, a treatment plan for the patient according to the principles of the present disclosure.

FIG. 6 generally illustrates an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the exercise apparatus 70 for 30 minutes 5 times a week for 3 weeks, wherein values for the properties, configurations, and/or settings of the exercise apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan or a variety of possible treatment plans for selection by a healthcare provider that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan or plans 602. In some embodiments, the machine learning model 13 may be trained to output one or more excluded treatment plans that should not be performed by the new patient.

Figure 7:
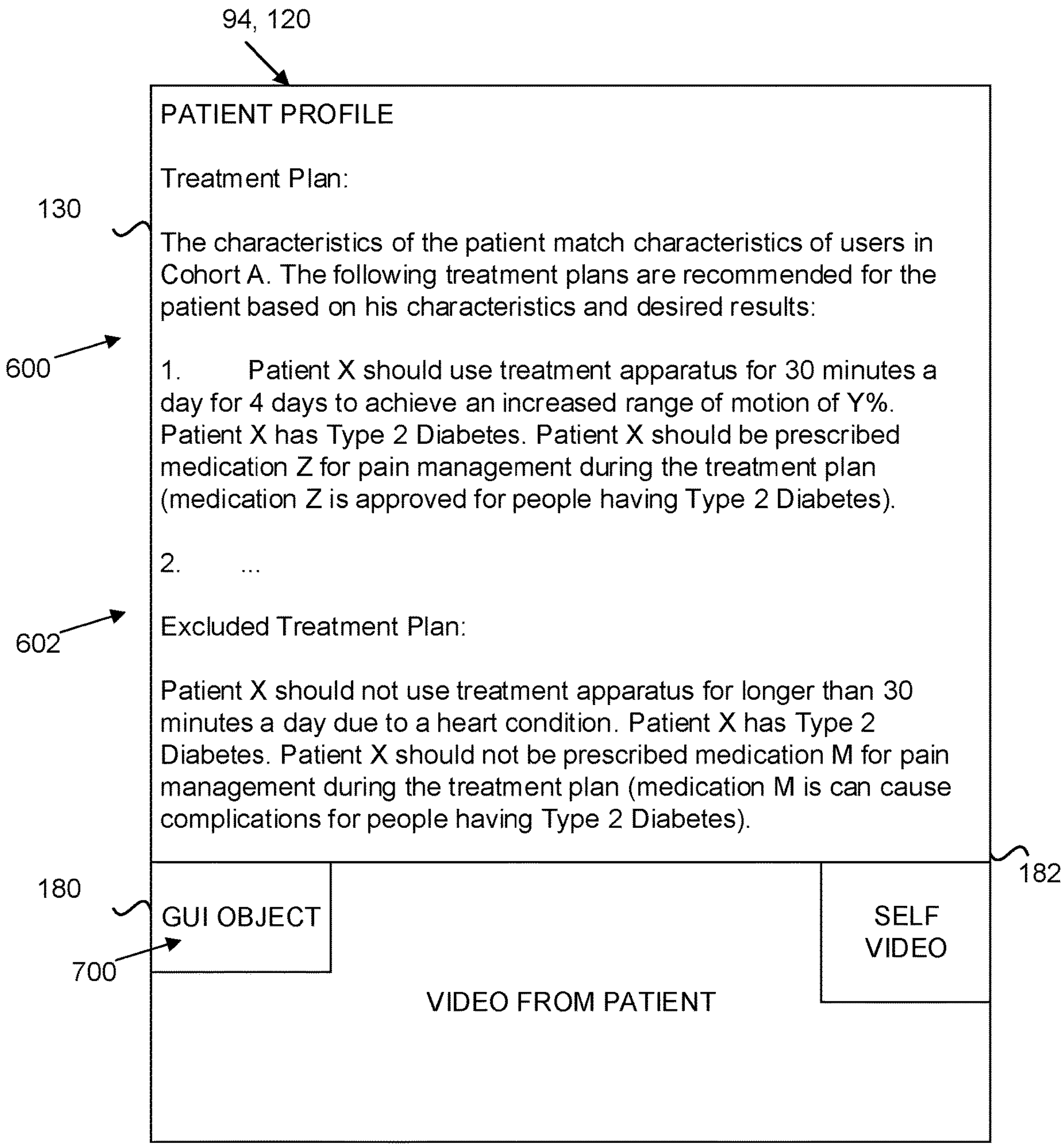
FIG. 7 generally illustrates an embodiment of an overview display of the assistant interface presenting recommended treatment plans and excluded treatment plans in real-time during a telemedicine session according to the principles of the present disclosure.

FIG. 7 generally illustrates an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare professional using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share, in real-time or near real-time during the telemedicine session, the recommended treatment plans and/or the excluded treatment plans with the patient on the patient interface 50. The healthcare professional may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the exercise apparatus 70 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of users in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for an exercise apparatus 70, a different medication regimen, etc.

As depicted, the patient profile display 130 may also present the excluded treatment plans 602. These types of treatment plans are shown to the healthcare professional using the assistant interface 94 to alert the healthcare professional not to recommend certain portions of a treatment plan to the patient. For example, the excluded treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare professional may select the treatment plan for the patient on the overview display 120. For example, the healthcare professional may use an input peripheral (e.g., mouse, touchscreen, microphone, keyboard, etc.) to select from the treatment plans 600 for the patient. In some embodiments, during the telemedicine session, the healthcare professional may discuss the pros and cons of the recommended treatment plans 600 with the patient.

In any event, the healthcare professional may select the treatment plan for the patient to follow to achieve the desired result. The selected treatment plan may be transmitted to the patient interface 50 for presentation. The patient may view the selected treatment plan on the patient interface 50. In some embodiments, the healthcare professional and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the exercise apparatus 70 as the user uses the exercise apparatus 70.

Figure 8:
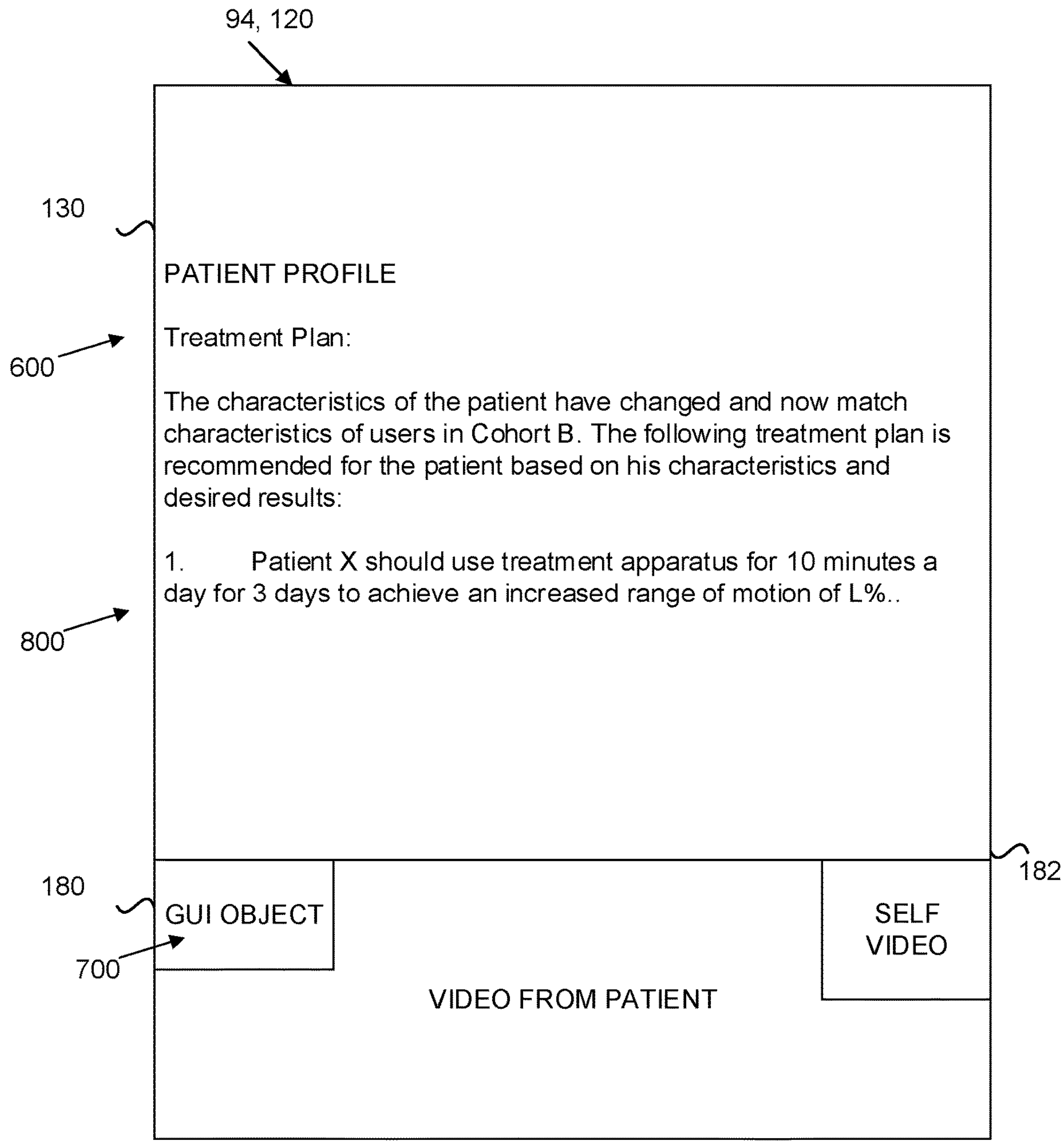
FIG. 8 generally illustrates an embodiment of the overview display of the assistant interface presenting, in real-time during a telemedicine session, recommended treatment plans that have changed as a result of patient data changing according to the principles of the present disclosure.

FIG. 8 generally illustrates an embodiment of the overview display 120 of the assistant interface 94 presenting, in real-time during a telemedicine session, recommended treatment plans that have changed as a result of patient data changing according to the present disclosure. As may be appreciated, the exercise apparatus 70 and/or any computing device (e.g., patient interface 50) may transmit data while the patient uses the exercise apparatus 70 to perform a treatment plan. The data may include updated characteristics of the patient and/or other treatment data. For example, the updated characteristics may include new performance information and/or measurement information. The performance information may include a speed of a portion of the exercise apparatus 70, a range of motion achieved by the patient, a force exerted on a portion of the exercise apparatus 70, a heartrate of the patient, a blood pressure of the patient, a respiratory rate of the patient, and so forth.

In some embodiments, the data received at the server 30 may be input into the trained machine learning model 13, which may determine that the characteristics indicate the patient is on track for the current treatment plan. Determining the patient is on track for the current treatment plan may cause the trained machine learning model 13 to adjust a parameter of the exercise apparatus 70. The adjustment may be based on a next step of the treatment plan to further improve the performance of the patient.

In some embodiments, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 13 may determine that the characteristics of the patient no longer match the characteristics of the patients in the cohort to which the patient is assigned. Accordingly, the trained machine learning model 13 may reassign the patient to another cohort that includes qualifying characteristics the patient's characteristics. As such, the trained machine learning model 13 may select a new treatment plan from the new cohort and control, based on the new treatment plan, the exercise apparatus 70.

In some embodiments, prior to controlling the exercise apparatus 70, the server 30 may provide the new treatment plan 800 to the assistant interface 94 for presentation in the patient profile 130. As depicted, the patient profile 130 indicates "The characteristics of the patient have changed and now match characteristics of users in Cohort B. The following treatment plan is recommended for the patient based on his characteristics and desired results." Then, the patient profile 130 presents the new treatment plan 800 ("Patient X should use the exercise apparatus 70 for 10 minutes a day for 3 days to achieve an increased range of motion of L %" The healthcare professional may select the new treatment plan 800, and the server 30 may receive the selection. The server 30 may control the exercise apparatus 70 based on the new treatment plan 800. In some embodiments, the new treatment plan 800 may be transmitted to the patient interface 50 such that the patient may view the details of the new treatment plan 800.

Figure 9:
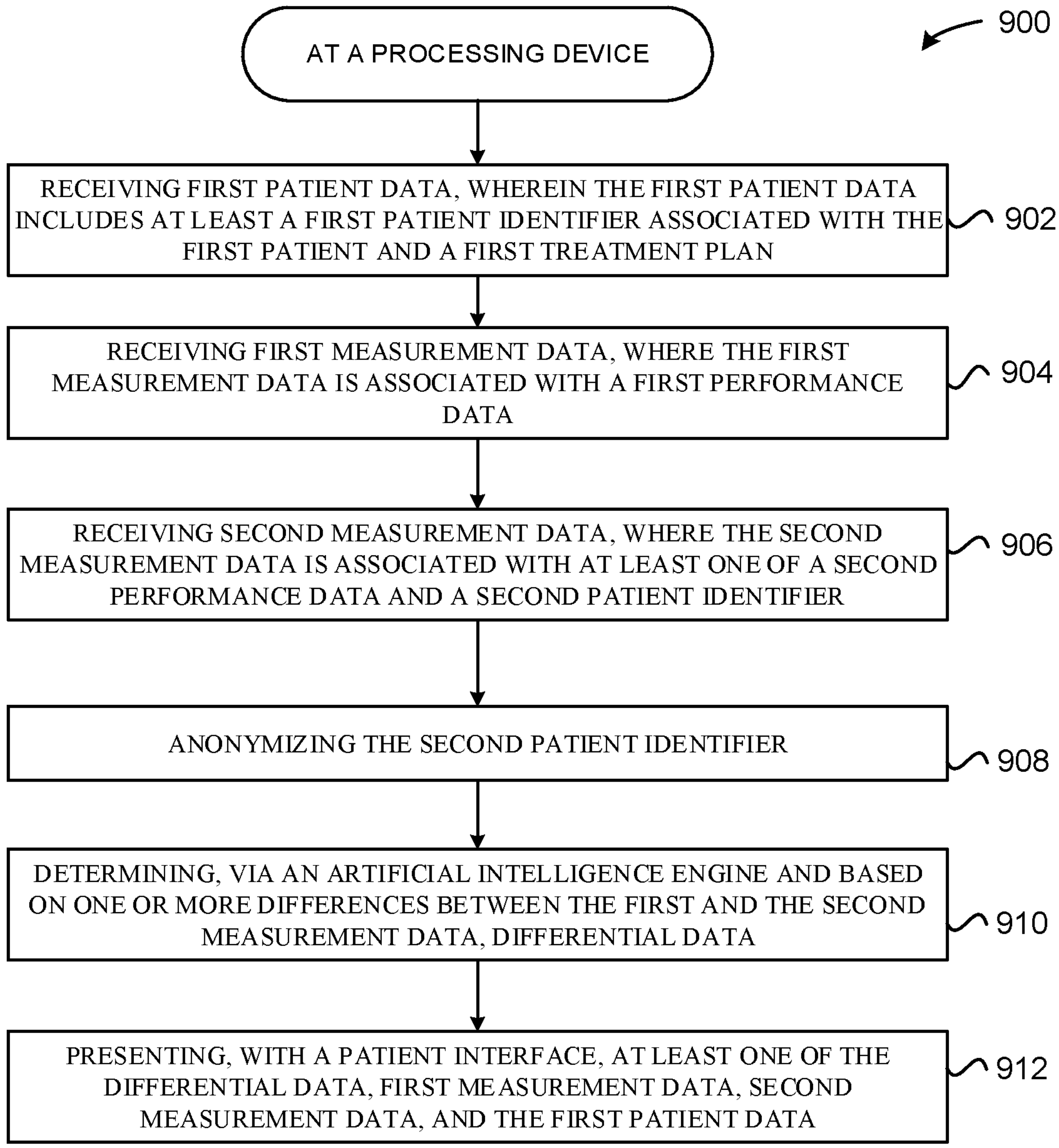
FIG. 9 is a flow diagram generally illustrating a method for performing an exercise with an exercise apparatus.

With reference to FIG. 9, the present disclosure further provides a method 900 for performing an exercise with an exercise apparatus. The method 900 comprises the step 902 of receiving first patient data, wherein the first patient data includes at least a first patient identifier associated with the first patient and a first treatment plan including an exercise. The patient data may be generated via the AI engine and associated with at least one of a prior exercise or a concurrent exercise.

The method 900 comprises the step 904 of receiving first measurement data, where the first measurement data is associated with a first performance data. The method 900 comprises the step 906 of receiving second measurement data, where the second measurement data is associated with at least one of a second performance data and a second patient identifier. The second measurement data may be generated via the AI engine and based on a statistic related to or derived from performance data of a cohort of patients. The characteristic may be generated via the AI engine and based on data from the cohort of patients. The second measurement data may also be received in real-time or near real-time.

The method 900 comprises the step 908 of one of anonymiztion of and pseudonymization of the second patient identifier. The method 900 comprises the step 910 of determining, via an artificial intelligence engine and based on one or more differences between the first and the second measurement data, differential data. The one or more differences may comprise one or more qualitative or quantitative differences. The method 900 comprises the step 912 of presenting, with a patient interface, at least one of the differential data, first measurement data, second measurement data, and the first patient data.

The method 900 may further comprise the step of modifying, via an artificial intelligence engine and based on the differential data, an operating parameter of the exercise apparatus. The method 900 may further comprise the step of controlling the first exercise apparatus. The method 900 may further comprise the step of transmitting an instruction, and wherein, further, the instruction comprises modifying an operating state of the exercise apparatus. The transmitting an instruction may further comprise transmitting, to the user interface, an input, and wherein, the input is displayed in the user interface. The method of claim 1, wherein the second measurement data is generated via the AI engine and based on a statistic related to or derived from performance data of a cohort of patients.

In some embodiments, the server 30 described herein may be configured for optimizing at least one exercise for a user. An exercise apparatus may be configured to enable the user to perform the at least one exercise. In some embodiments, the server 30 described herein may be configured to receive user data. The user data may include attribute data associated with the user and outcome data associated with the exercise. The outcome data may be based on a selection by the user. The outcome data may be generated, based on the machine learning model, by the artificial intelligence engine. The attribute of the user may comprise at least one of a measurement of a vital sign of the user, a respiration rate of the user, a heartrate of the user, a heart rhythm of a user, an oxygen saturation of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the exercise apparatus, an amount of force exerted on a portion of the exercise apparatus, a range of motion achieved on the exercise apparatus, a movement speed of a portion of the exercise apparatus, a pressure exerted on a portion of the exercise apparatus, a movement acceleration of a portion of the exercise apparatus, a movement jerk of a portion of the exercise apparatus, a torque level of a portion of the exercise apparatus, and an indication of a plurality of pain levels experienced by the user when using the exercise apparatus.

In some embodiments, the server 30 described herein may be configured to generate, based on the user data, initial target data. The initial target data may be associated with at least one of the user, the exercise apparatus, and the exercise.

In some embodiments, the server 30 described herein may be configured to receive measurement data associated with at least one of the user, the exercise apparatus, and the exercise. The measurement data may be associated with one or more sensors. The measurement data may be sensor data received from one or more sensors associated with at least one of the user, the exercise apparatus, and the exercise. The measurement data may be received in real-time or near real-time. The outcome data may include at least one of a duration of the exercise, a duration of uninterrupted use, a weight, a number of repetitions, a respiration rate of the user, a heartrate of the user, a reaction time, a perspiration rate of the user, an amount of force exerted on a portion of the exercise apparatus, a range of motion achieved on the exercise apparatus, a pressure exerted on a portion of the exercise apparatus, a movement speed of a portion of the exercise apparatus, a movement acceleration of a portion of the exercise apparatus, a movement jerk of a portion of the exercise apparatus, a torque level of a portion of the exercise apparatus, or any combination thereof.

In some embodiments, the server 30 described herein may be configured to determine differential data. The determining may be based on one or more differences between the initial target data and the measurement data. In some embodiments, the server 30 described herein may be configured to receive, based on cohort users who perform the exercise, cohort data.

In some embodiments, the server 30 described herein may be configured to generate, via an artificial intelligence engine and based on the differential data, a machine learning model trained to generate message data based on a difference between the differential data and the cohort data. The message data may comprise at least one of audio data, visual data, and haptic data.

The audio data may include a verbal characteristic associated with at least one of a volume, a cadence, a tone, an enunciation, a word, a language, a dialect, a vernacular, an accent, an emphasis, a pitch, a rhythm, an order of words, a tense, a timbre, and a prosody. The verbal characteristic may be based on at least one of the cohort data and the outcome data. The visual data may include a visual characteristic associated with at least one of a color, an image, a video, a text, a font type, a font style, a point size, a font modifier, a virtual-reality environment, and an illumination. The visual characteristic may be based on at least one of the cohort data and the outcome data. The haptic data may include a haptic characteristic associated with at least one of a vibration, a force, a pressure, a torque, an intensity, a resistance, an electric stimulus, an ultrasonic frequency, a heat level, and a temperature. The haptic characteristic may be based on at least one of the cohort data and the outcome data.

It should be appreciated that, according to some embodiments, optimization of the at least one exercise is achieved by motivating via positive or negative feedback, the user of the exercise apparatus 70. This may be accomplished via the particular message that is transmitted to the interface. For example, if the user is partially blind, the message may not include textual elements, but rather will include an audio and haptic element in order to alert the user to his status. In this particular example, if the user is pedaling the exercise apparatus 70 too slowly according to the measurement data relative to the outcome data, the message transmitted may audibly say, in a deep intense voice "Keep going, you can do it!" Alternatively, if the user has hearing trouble, the message may instead output on the interface a bolded and underlined textual message of similar terms. Additionally or alternatively, the user interface may display a red color with flashing elements, or alternatively may display an image of an avatar speaking the textual message. In some embodiments, a video message may be displayed on the interface with the video including an avatar teaching the user how to increase efficiency of the exercise.

It should further be appreciated that, according to some embodiments, optimization of the at least one exercise is achieved by monitoring the response of the user after the message is transmitted to the interface. In other words, in some embodiments, not only does the user receive the most optimal message available in the system, but the optimal message is continuously updated based on the response the user has to the optimal message. As such, the message may be actively refined over time with the machine learning model 13 being trained based on the response times of previous users with various conditions. For example, based on cohort data, the machine learning model 13 may identify via correlation that certain conditions of a user produce certain measurement data consistently, despite the correlation being unnoticed or undetectable by a human observer. In addition, the machine learning model 13 may identify specific types of feedback in the message that are likely to induce a particular response by the user. Unexpected responses to the message may further allow the machine learning model 13 to try different forms of feedback to identify another condition of the user. For example, if it is determined that the best message to output is an audible one with a high degree of intensity, but outputting that message does not achieve the desired outcome, the machine learning model may detect that the user may suffer from hearing loss.

In some embodiments, the at least one exercise, including the configurations, settings, range of motion settings, pain level, force settings, and speed settings, etc. of the exercise apparatus 70 for various exercises, may be transmitted to the controller of the exercise apparatus 70. In one example, if the user provides an indication, via the patient interface 50, that he is experiencing a high level of pain at a particular range of motion, the controller may receive the indication. Based on the indication, the controller may electronically adjust the range of motion of the pedal 102 by adjusting the pedal inwardly, outwardly, or along or about any suitable axis, via one or more actuators, hydraulics, springs, electric motors, or the like. The at least one exercise may define alternative range of motion settings for the pedal 102 when the user indicates certain pain levels during an exercise. Accordingly, once the at least one exercise is uploaded to the controller of the exercise apparatus 70, the exercise apparatus 70 may continue to operate without further instruction, further external input, and the like. It should be noted that the user (via the patient interface 50) and/or the assistant (via the assistant interface 94) may override any of the configurations or settings of the exercise apparatus 70 at any time. For example, the user may use the patient interface 50 to cause the exercise apparatus 70 to immediately stop, if so desired.

Figure 10:
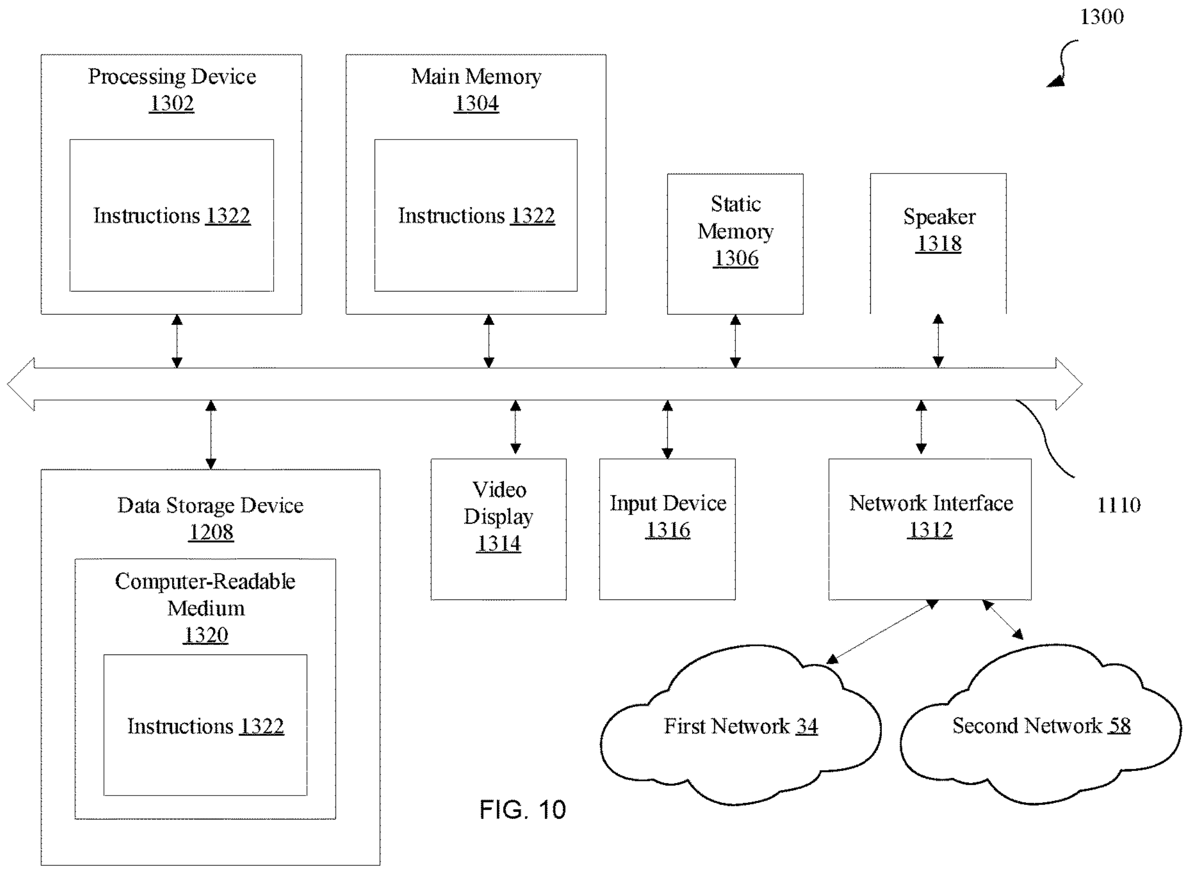
FIG. 10 generally illustrates a computer system according to the principles of the present disclosure.

FIG. 10 shows an example computer system 1300, which can perform any one or more of the methods described herein, in accordance with one or more aspects of the present disclosure. In one example, computer system 1300 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1300 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1300 includes a processing device 1302, a main memory 1304 (e.g., read-only memory (ROM), flash memory, solid state drives (SSDs), dynamic random access memory (DRAM) such as synchronous DRAM (SDRAM)), a static memory 1306 (e.g., flash memory, solid state drives (SSDs), static random access memory (SRAM)), and a data storage device 1308, which communicate with each other via a bus 1310.

Processing device 1302 represents one or more general-purpose processing devices such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1302 may also be one or more special-purpose processing devices such as an application specific integrated circuit (ASIC), a system on a chip, a field programmable gate array (FPGA), a digital signal processor (DSP), network processor, or the like. The processing device 102 is configured to execute instructions for performing any of the operations and steps discussed herein.

The computer system 1300 may further include a network interface device 1312. The computer system 1300 also may include a video display 1314 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1316 (e.g., a keyboard and/or a mouse or a gaming-like control), and one or more speakers 1318 (e.g., a speaker). In one illustrative example, the video display 1314 and the input device(s) 1316 may be combined into a single component or device (e.g., an LCD touch screen).

The data storage device 1316 may include a computer-readable medium 1320 on which the instructions 1322 embodying any one or more of the methods, operations, or functions described herein is stored. The instructions 1322 may also reside, completely or at least partially, within the main memory 1304 and/or within the processing device 1302 during execution thereof by the computer system 1300. As such, the main memory 1304 and the processing device 1302 also constitute computer-readable media. The instructions 1322 may further be transmitted or received over a network via the network interface device 1312.

While the computer-readable storage medium 1420 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for performing an exercise with an exercise apparatus, the method comprising: receiving first patient data, wherein the first patient data includes at least a first patient identifier associated with the first patient and a first treatment plan including an exercise; receiving first measurement data, where the first measurement data is associated with a first performance data; receiving second measurement data, where the second measurement data is associated with at least one of a second performance data and a second patient identifier; one of anonymiztion of and pseudonymization of the second patient identifier; determining, via an artificial intelligence engine and based on one or more differences between the first and the second measurement data, differential data; and presenting, with a patient interface, at least one of the differential data, first measurement data, second measurement data, and the first patient data.

Clause 2. The method of Clause 1, further comprising modifying, via an artificial intelligence engine and based on the differential data, an operating parameter of the exercise apparatus.

Clause 3. The method of Clause 3, further comprising controlling the first exercise apparatus.

Clause 4. The method of Clause 3, wherein controlling comprises transmitting an instruction, and wherein, further, the instruction comprises modifying an operating state of the exercise apparatus.

Clause 5. The method of Clause 4, wherein transmitting an instruction further comprises transmitting, to the user interface, an input, and wherein, the input is displayed in the user interface.

Clause 6. The method of Clause 1, wherein the one or more differences comprises one or more qualitative differences.

Clause 7. The method of Clause 1, wherein the one or more differences comprises one or more quantitative differences.

Clause 8. The method of Clause 4, wherein the first patient data is generated via the AI engine and associated with at least one of a prior exercise and a concurrent exercise.

Clause 9. The method of Clause 1, wherein the second measurement data is generated via the AI engine and based on a statistic related to or derived from performance data of a cohort of patients.

Clause 10. The method of Clause 9, wherein the second measurement data is associated with a characteristic generated via the AI engine and based on the performance data of the cohort of patients.

Clause 11. The method of Clause 9, wherein the characteristic is generated via the AI engine and based on data from the cohort of patients.

Clause 12. The method of Clause 11, wherein the second measurement data is received in real-time or near real-time.

Clause 13. A system for performing an exercise with an exercise apparatus, the system comprising: a processing device; an artificial intelligence engine communicatively coupled to the processing device; a memory including instruction that, when executed by the processing device, cause the processing device to: receive first patient data, wherein the first patient data includes at least a first patient identifier associated with the first patient and a first treatment plan including an exercise; receive first measurement data, where the first measurement data is associated with a first performance data; receive second measurement data, where the second measurement data is associated with at least one of a second performance data and a second patient identifier; anonymize the second patient identifier; and determine, via an artificial intelligence engine and based on one or more differences between the first and the second measurement data, differential data; and present, with a patient interface, a least one of the differential data, first measurement data, second measurement data, and the first patient data.

Clause 14. The system of Clause 13, wherein the processing device is further configured to modify, via an artificial intelligence engine and based on the differential data, an operating parameter of the exercise apparatus.

Clause 15. The system of Clause 14, wherein the processing device is further configured to control the first exercise apparatus.

Clause 16. The system of Clause 15, wherein controlling comprises transmitting an instruction, and wherein, further, the instruction comprises modifying an operating state of the exercise apparatus.

Clause 17. The system of Clause 15, wherein transmitting an instruction further comprises transmitting, to the user interface, an input, and wherein, the input is displayed in the user interface.

Clause 18. The system of Clause 15, wherein the first patient data is generated via the AI engine and associated with at least one of a prior exercise and a concurrent exercise.

Clause 19. The system of Clause 13, wherein the second measurement data is generated via the AI engine and based on a statistic related to or derived from performance data of a cohort of patients.

Clause 20. The system of Clause 19, wherein the second measurement data is associated with a characteristic generated via the AI engine and based on the performance data of the cohort of patients.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method for performing an exercise with an exercise apparatus, the method comprising:

receiving first patient data, wherein the first patient data includes at least a first patient identifier associated with the first patient and a first treatment plan including an exercise, wherein the first treatment plan is generated by one or more computer-implemented models trained using training data comprising inputs mapped to outputs, wherein the inputs are associated with medical conditions of users and the outputs are associated with treatment plans;

receiving first measurement data, wherein the first measurement data is associated with a first performance data;

receiving second measurement data, wherein the second measurement data is associated with at least one of a second performance data and a second patient identifier;

performing one of anonymization of and pseudonymization of the second patient identifier;

determining, via an artificial intelligence (AI) engine and based on one or more differences between the first and the second measurement data, differential data;

presenting, with a patient interface, at least one of the differential data, first measurement data, second measurement data, and the first patient data;

based on the first treatment plan, controlling, via the one or more computer-implemented models, the exercise apparatus by automatically modifying an operating parameter of a physical portion of the exercise apparatus.

2. The method of claim 1, further comprising modifying, via the AI engine and based on the differential data, an operating parameter of the exercise apparatus.

3. The method of claim 2, wherein controlling comprises transmitting an instruction, and wherein, further, the instruction comprises modifying an operating state of the exercise apparatus.

4. The method of claim 3, wherein transmitting an instruction further comprises transmitting, to the user interface, an input, and wherein, the input is displayed in the user interface.

5. The method of claim 3, wherein the first patient data is generated via the AI engine and associated with at least one of a prior exercise and a concurrent exercise.

6. The method of claim 1, wherein the one or more differences comprises one or more qualitative differences.

7. The method of claim 1, wherein the one or more differences comprises one or more quantitative differences.

8. The method of claim 1, wherein the second measurement data is generated via the AI engine and based on a statistic related to or derived from performance data of a cohort of patients.

9. The method of claim 8, wherein the second measurement data is associated with a characteristic generated via the AI engine and based on the performance data of the cohort of patients.

10. The method of claim 9, wherein the characteristic is generated via the AI engine and based on data from the cohort of patients.

11. The method of claim 10, wherein the second measurement data is received in real-time or near real-time.

12. A system for performing an exercise with an exercise apparatus, the system comprising:

a processing device;

an artificial intelligence (AI) engine executed by the processing device;

a memory including instruction that, when executed by the processing device, cause the processing device to:

receive first patient data, wherein the first patient data includes at least a first patient identifier associated with the first patient and a first treatment plan including an exercise, wherein the first treatment plan is generated by one or more computer-implemented models trained using training data comprising inputs mapped to outputs, wherein the inputs are associated with medical conditions of users and the outputs are associated with treatment plans;

receive first measurement data, where the first measurement data is associated with a first performance data;

receive second measurement data, where the second measurement data is associated with at least one of a second performance data and a second patient identifier;

anonymize the second patient identifier;

determine, via the artificial intelligence engine and based on one or more differences between the first and the second measurement data, differential data;

present, with a patient interface, at least one of the differential data, first measurement data, second measurement data, and the first patient data; and based on the first treatment plan, control, via the one or more computer-implemented models, the exercise apparatus by automatically modifying an operating parameter of a physical portion of the exercise apparatus.

13. The system of claim 12, wherein the processing device is further configured to modify, via the AI engine and based on the differential data, an operating parameter of the exercise apparatus.

14. The system of claim 13, wherein transmitting an instruction further comprises transmitting, to the user interface, an input, and wherein, the input is displayed in the user interface.

15. The system of claim 13, wherein the first patient data is generated via the AI engine and associated with at least one of a prior exercise and a concurrent exercise.

16. The system of claim 13, wherein controlling comprises transmitting an instruction, and wherein, further, the instruction comprises modifying an operating state of the exercise apparatus.

17. The system of claim 12, wherein the second measurement data is generated via the AI engine and based on a statistic related to or derived from performance data of a cohort of patients.

18. The system of claim 17, wherein the second measurement data is associated with a characteristic generated via the AI engine and based on the performance data of the cohort of patients.

* * * * *